US012616505B2

(12) United States Patent
Harari et al.

(10) Patent No.: US 12,616,505 B2
(45) Date of Patent: May 5, 2026

---

(54) ACCORDION MANEUVER WITH A BONE FIXATION DEVICE

(71) Applicant: Synthes GmbH, Oberdorf (CH)

(72) Inventors: Shahar Harari, Tel-Aviv (IL); Oren Cohen, Moreshet (IL); Michael Wahl, Raynham, MA (US); Scott P. Lavoritano, West Chester, PA (US); Albert A. Montello, West Chester, PA (US)

(73) Assignee: Synthes GmbH, Oberdorf (CH)

( * ) Notice: Subject to any disclaimer, the term of this patent is extended or adjusted under 35 U.S.C. 154(b) by 0 days.

(21) Appl. No.: 18/785,431

(22) Filed: Jul. 26, 2024

(65) Prior Publication Data

US 2025/0064484 A1 Feb. 27, 2025

(51) Int. Cl.
*A61B 17/66* (2006.01)
*A61B 5/00* (2006.01)
(Continued)

(52) U.S. Cl.
CPC .............. *A61B 17/66* (2013.01); *A61B 34/10* (2016.02); *A61B 5/6811* (2013.01);
(Continued)

(58) Field of Classification Search
CPC ....... A61B 17/62; A61B 17/66; A61B 17/663; A61B 17/60; A61B 17/645; A61B 17/58;
(Continued)

(56) References Cited

U.S. PATENT DOCUMENTS 5,180,380 A * 1/1993 Pursley .............. A61B 17/7216
606/56
5,437,668 A * 8/1995 Aronson ................ A61B 17/62
606/56
(Continued)

FOREIGN PATENT DOCUMENTS

AU 2020354546 A1 3/2022
CN 106413604 A 2/2017
(Continued)

OTHER PUBLICATIONS

Makhdom, et al. "The Accordion Maneuver: A Noninvasive Strategy for Absent or Delayed Callus Formation in Cases of Limb Lengthening", Hindawi Publishing Corporation, Advances in Orthopedics, vol. 2015, Article ID 912790, 8 pages.
(Continued)

*Primary Examiner* — Marcela I. Shirsat
(74) *Attorney, Agent, or Firm* — Flaster Greenberg P.C.

(57) ABSTRACT

A control system for use with an adjustable bone fixation device including a first fixation element and a second fixation element connectable to bone tissue portions on either side of a treatment site, the control system including: one or more actuators configured to controllably adjust lengths of a plurality of adjustable length struts of the bone fixation device, the plurality of adjustable length struts connecting the first and the second fixation elements of the bone fixation device, length adjustment thereof changing a spatial relationship between the first and the second fixation elements; and circuitry configured to control the one or more actuators to cause the first and second fixation elements to perform an accordion maneuver by performing a plurality of actuations to adjust lengths of the plurality of adjustable length struts to create a reciprocal movement of the first and second fixation elements relative to each other.

20 Claims, 14 Drawing Sheets

(51) Int. Cl.

| | |
|---|---|
| *A61B 17/00* | (2006.01) |
| *A61B 17/17* | (2006.01) |
| *A61B 17/56* | (2006.01) |
| *A61B 17/60* | (2006.01) |
| *A61B 17/62* | (2006.01) |
| *A61B 17/64* | (2006.01) |
| *A61B 17/88* | (2006.01) |
| *A61B 34/00* | (2016.01) |
| *A61B 34/10* | (2016.01) |
| *A61B 34/32* | (2016.01) |

(52) U.S. Cl.
CPC ... *A61B 5/6812* (2013.01); *A61B 2017/00022* (2013.01); *A61B 2017/00075* (2013.01); *A61B 2017/00115* (2013.01); *A61B 2017/00123* (2013.01); *A61B 2017/00132* (2013.01); *A61B 17/171* (2013.01); *A61B 2017/564* (2013.01); *A61B 17/60* (2013.01); *A61B 17/62* (2013.01); *A61B 17/6425* (2013.01); *A61B 17/645* (2013.01); *A61B 17/6466* (2013.01); *A61B 17/88* (2013.01); *A61B 2034/104* (2016.02); *A61B 34/25* (2016.02); *A61B 34/32* (2016.02)

(58) Field of Classification Search
CPC . A61B 17/64; A61B 17/6425; A61B 17/6411; A61B 17/6466; A61B 17/171; A61B 17/88; A61B 2017/564; A61B 2017/00022; A61B 2017/00075; A61B 2017/00132; A61B 2017/00115; A61B 2017/00123; A61B 34/10; A61B 34/20; A61B 34/30; A61B 34/25; A61B 34/32; A61B 5/6812; A61B 5/6811; A61B 2034/104
USPC .......................... 606/56, 53, 54, 57, 58, 59
See application file for complete search history.

(56) References Cited

U.S. PATENT DOCUMENTS

| | | | | |
|---|---|---|---|---|
| 11,076,801 | B2 | 8/2021 | Cohen et al. | |
| 11,896,267 | B2 | 2/2024 | Pak et al. | |
| 2005/0043659 | A1* | 2/2005 | Challis | A61N 1/36003 |
| | | | | 602/5 |
| 2008/0051779 | A1* | 2/2008 | Mackenzie | A61B 17/62 |
| | | | | 606/57 |
| 2013/0041288 | A1* | 2/2013 | Taylor | A61B 5/6878 |
| | | | | 600/587 |
| 2017/0071632 | A1 | 3/2017 | Vikinsky et al. | |
| 2021/0027879 | A1* | 1/2021 | Noblett | A61B 17/66 |
| 2022/0346846 | A1 | 11/2022 | Pool | |
| 2023/0248393 | A1 | 8/2023 | Cheng et al. | |
| 2023/0255665 | A1 | 8/2023 | Pak et al. | |

FOREIGN PATENT DOCUMENTS

| | | | |
|---|---|---|---|
| WO | 2019195231 | A1 | 10/2019 |
| WO | 2020092049 | A1 | 5/2020 |
| WO | 2022024133 | A8 | 2/2022 |
| WO | 2023048948 | A1 | 3/2023 |
| WO | 2023163874 | A1 | 8/2023 |
| WO | 2023205046 | A1 | 10/2023 |
| WO | 2023230203 | A1 | 11/2023 |
| WO | 2023244586 | A1 | 12/2023 |
| WO | 2024059116 | A1 | 3/2024 |
| WO | 2024102351 | A1 | 5/2024 |
| WO | 2024102395 | A1 | 5/2024 |

OTHER PUBLICATIONS

Fu, et al. "Automated continuous distraction osteogenesis system for limb lengthening and reconstruction", IPEM—Translation, vol. 5, 2023, 100016, ISSN 2667-2588.

Bachmeier et al. "Novel approach to estimate distraction forces in distraction osteogenesis and application in the human lower leg", Journal of the Mechanical Behavior of Biomedical Materials, vol. 128, 2022, 105133, ISSN 1751-6161.

* cited by examiner

600

601

605

603

| | |
|---|---|
| Assess subject | 600 |
| Determine treatment including determining an actuation plan | 602 |
| Attach fixation elements to bone tissue | 604 |
| Install control system | 606 |
| Automatically perform actuation plan, e.g. including controlled accordion maneuver/s | 608 |

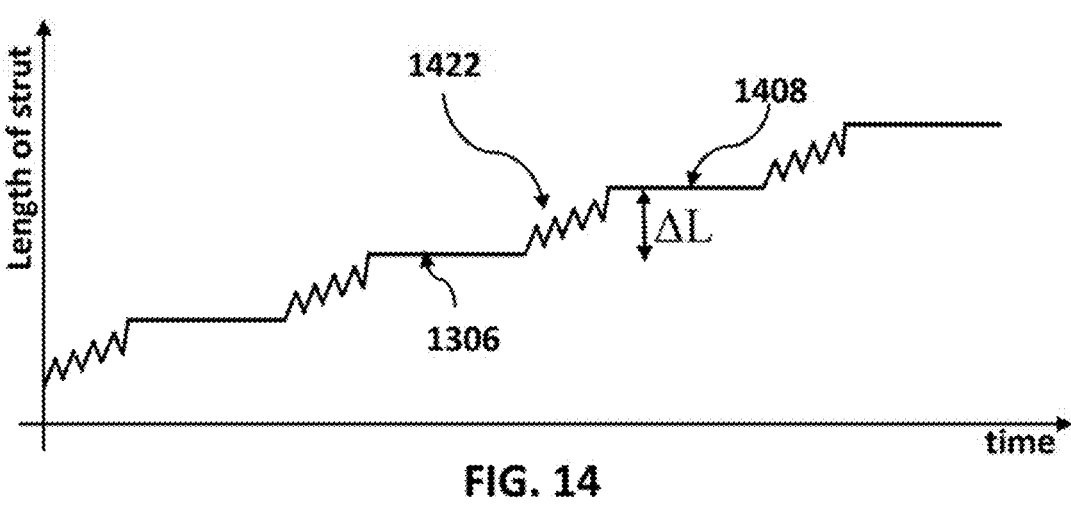
FIG. 14
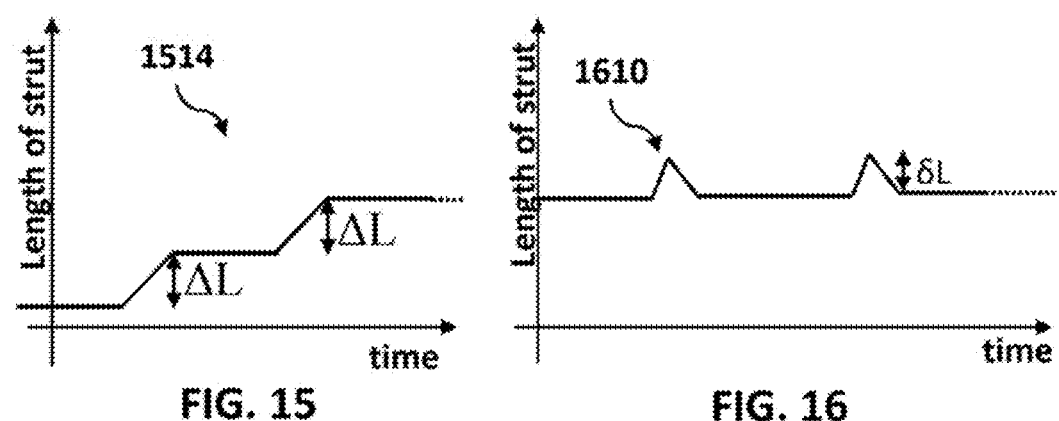
FIG. 15          FIG. 16
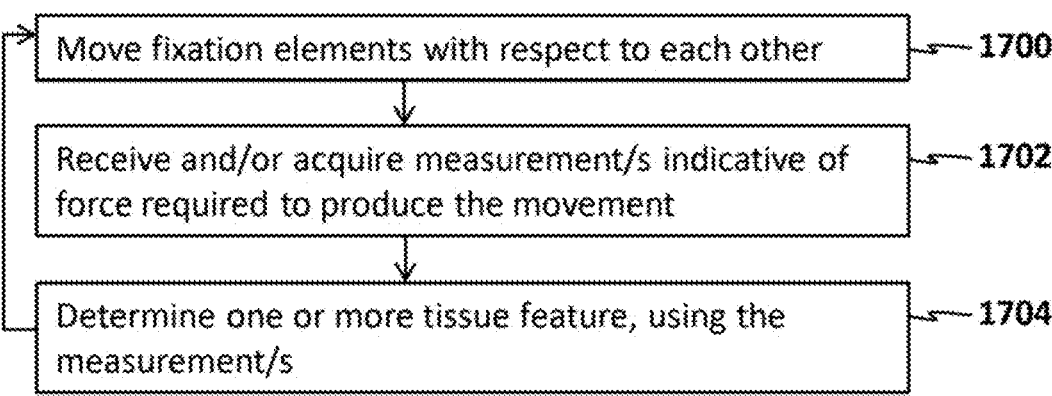
FIG. 17

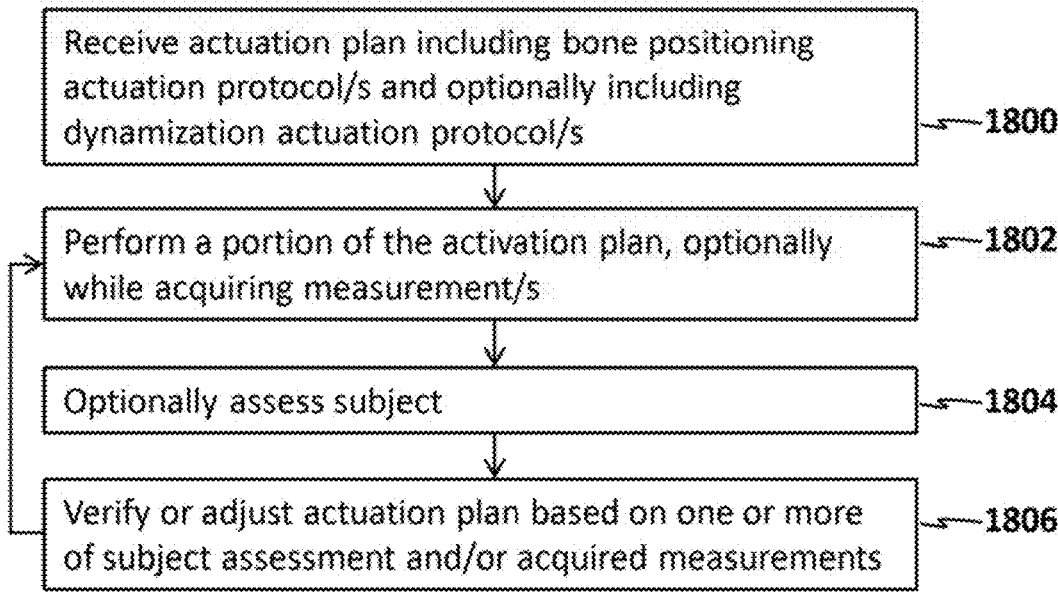

Receive actuation plan including bone positioning actuation protocol/s and optionally including dynamization actuation protocol/s —1800

Perform a portion of the activation plan, optionally while acquiring measurement/s —1802

Optionally assess subject —1804

Verify or adjust actuation plan based on one or more of subject assessment and/or acquired measurements —1806

FIG. 18

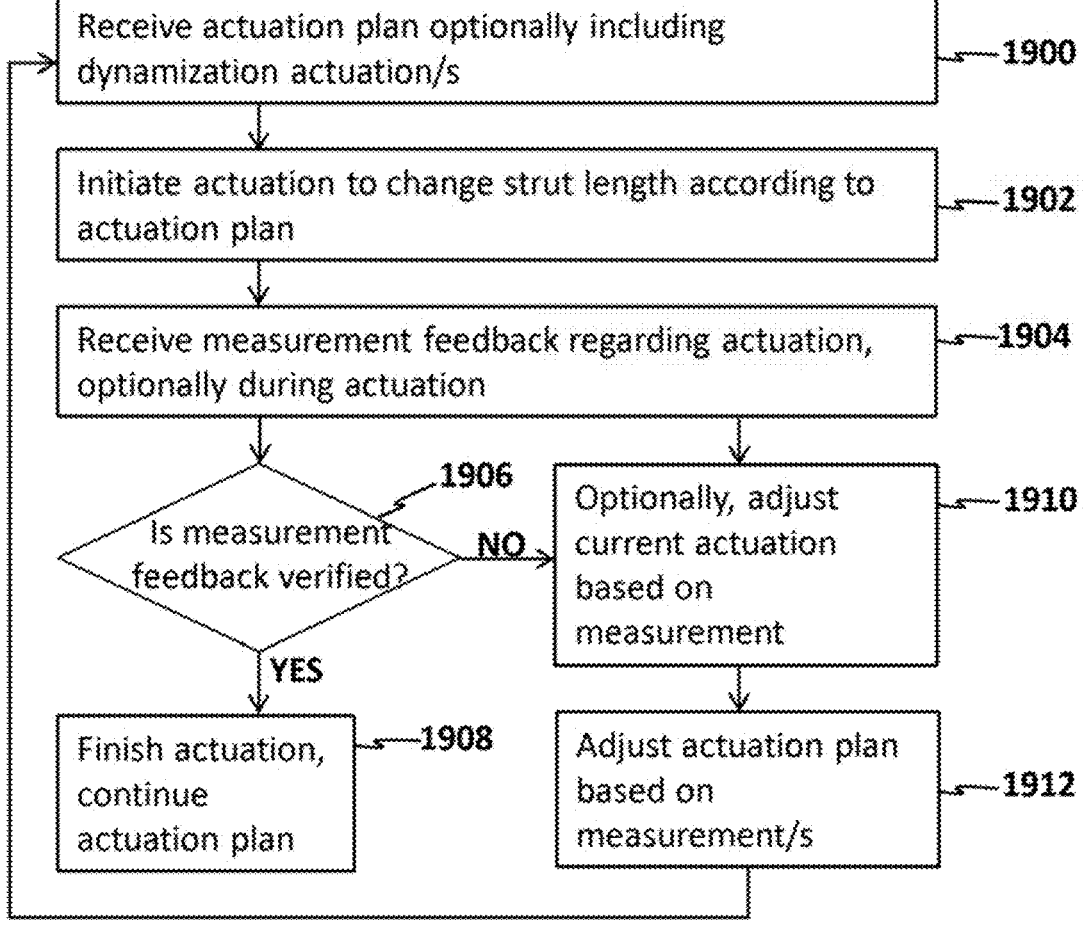

Receive actuation plan optionally including dynamization actuation/s —1900

Initiate actuation to change strut length according to actuation plan —1902

Receive measurement feedback regarding actuation, optionally during actuation —1904

Is measurement feedback verified? —1906

Optionally, adjust current actuation based on measurement —1910

YES

NO

Finish actuation, continue actuation plan —1908

Adjust actuation plan based on measurement/s —1912

FIG. 19

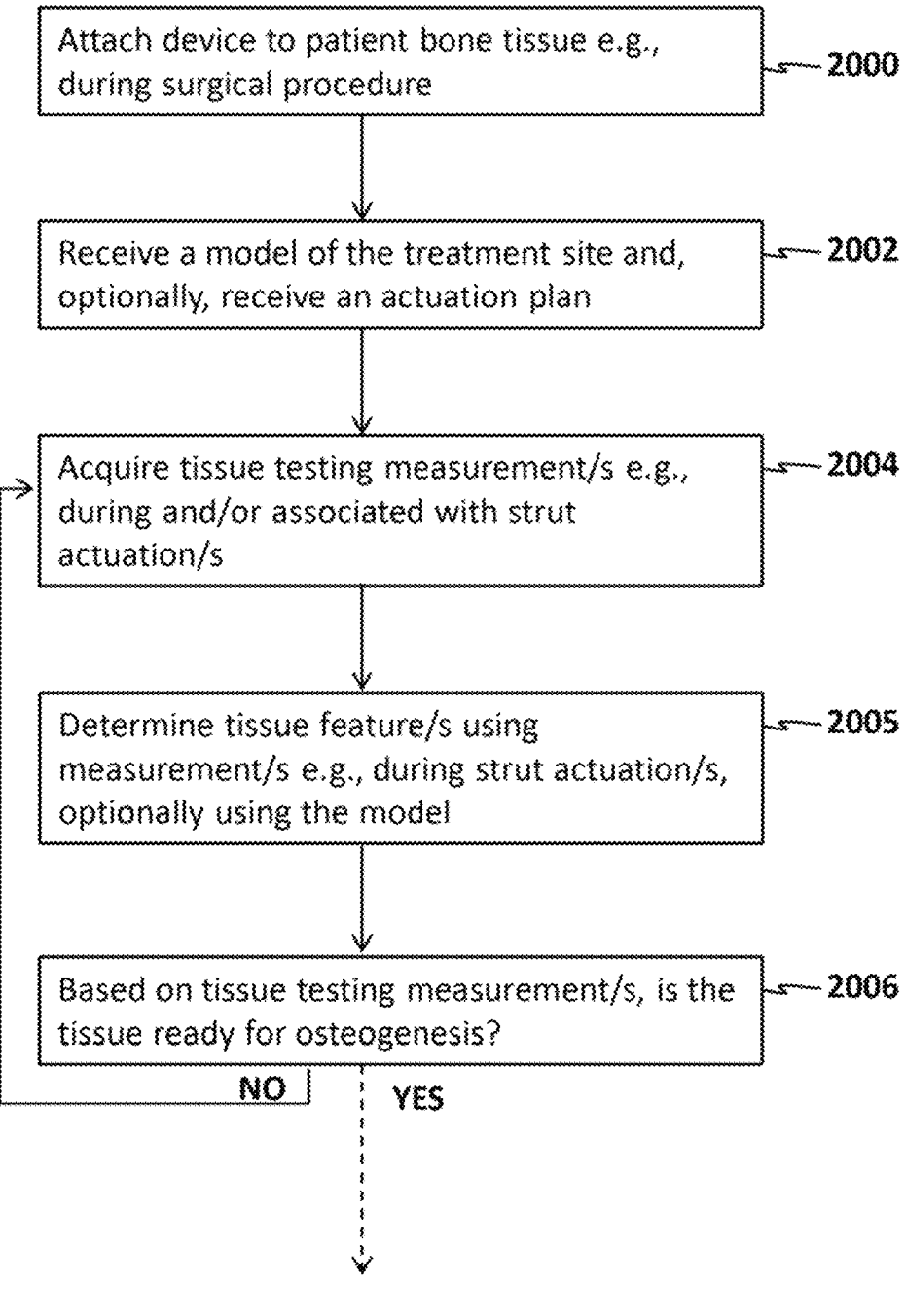

Attach device to patient bone tissue e.g., during surgical procedure ⟵ 2000

Receive a model of the treatment site and, optionally, receive an actuation plan ⟵ 2002

Acquire tissue testing measurement/s e.g., during and/or associated with strut actuation/s ⟵ 2004

Determine tissue feature/s using measurement/s e.g., during strut actuation/s, optionally using the model ⟵ 2005

Based on tissue testing measurement/s, is the tissue ready for osteogenesis? ⟵ 2006

NO                    YES

FIG. 20A

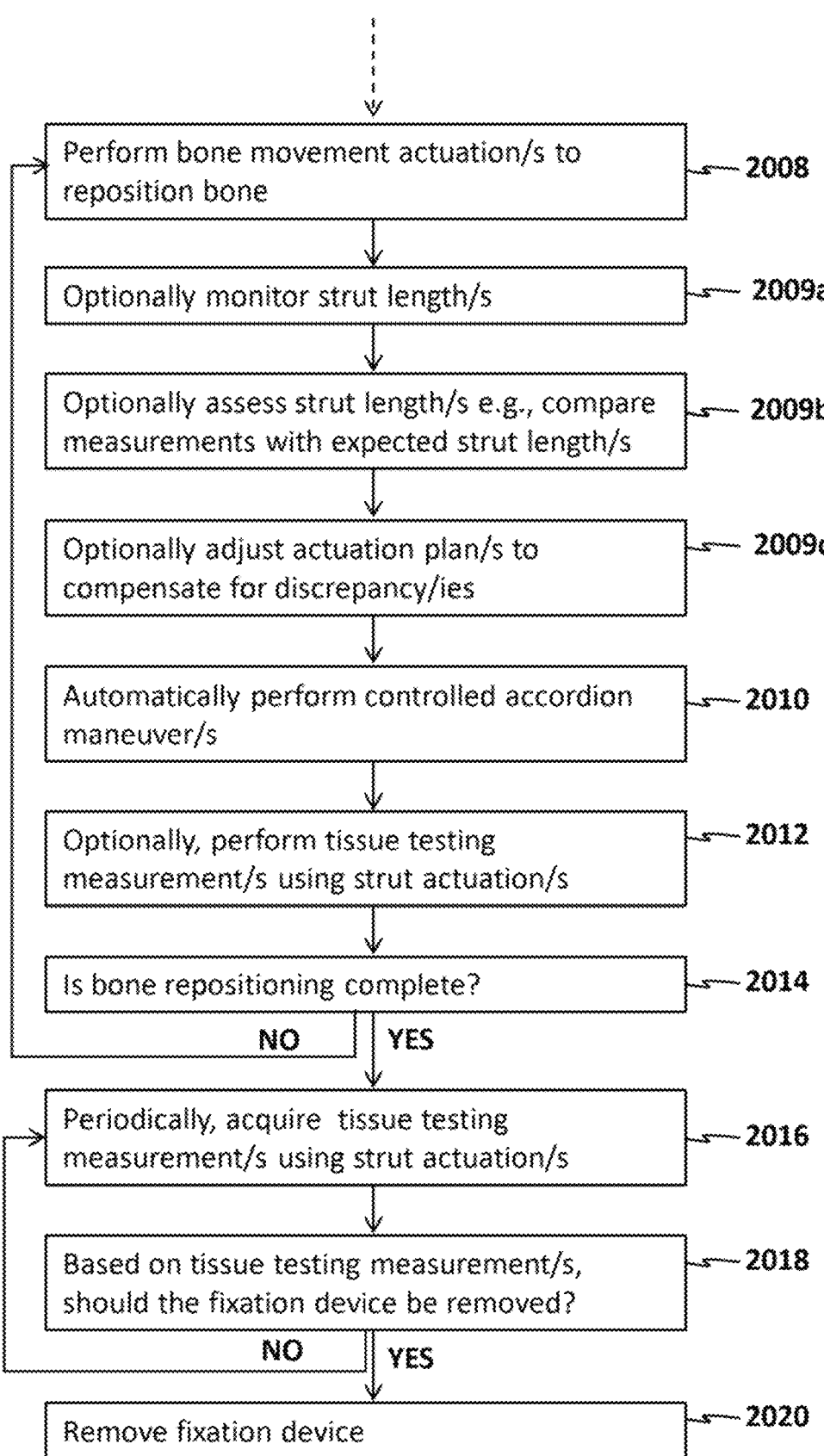

Perform bone movement actuation/s to reposition bone —— 2008

Optionally monitor strut length/s —— 2009a

Optionally assess strut length/s e.g., compare measurements with expected strut length/s —— 2009b Optionally adjust actuation plan/s to compensate for discrepancy/ies —— 2009c Automatically perform controlled accordion maneuver/s —— 2010

Optionally, perform tissue testing measurement/s using strut actuation/s —— 2012

Is bone repositioning complete? —— 2014

NO     YES

Periodically, acquire tissue testing measurement/s using strut actuation/s —— 2016

Based on tissue testing measurement/s, should the fixation device be removed? —— 2018

NO     YES

Remove fixation device —— 2020

FIG. 20B

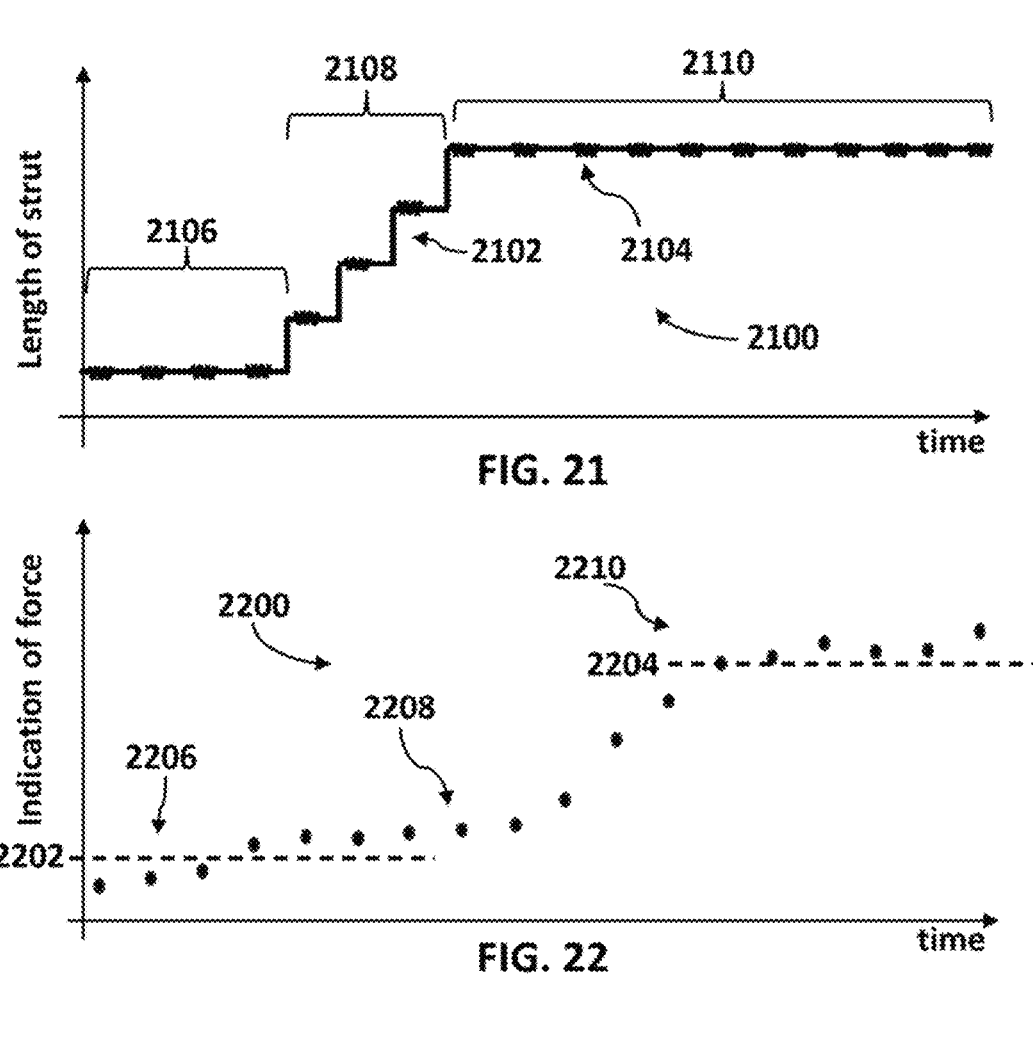
FIG. 21
FIG. 22
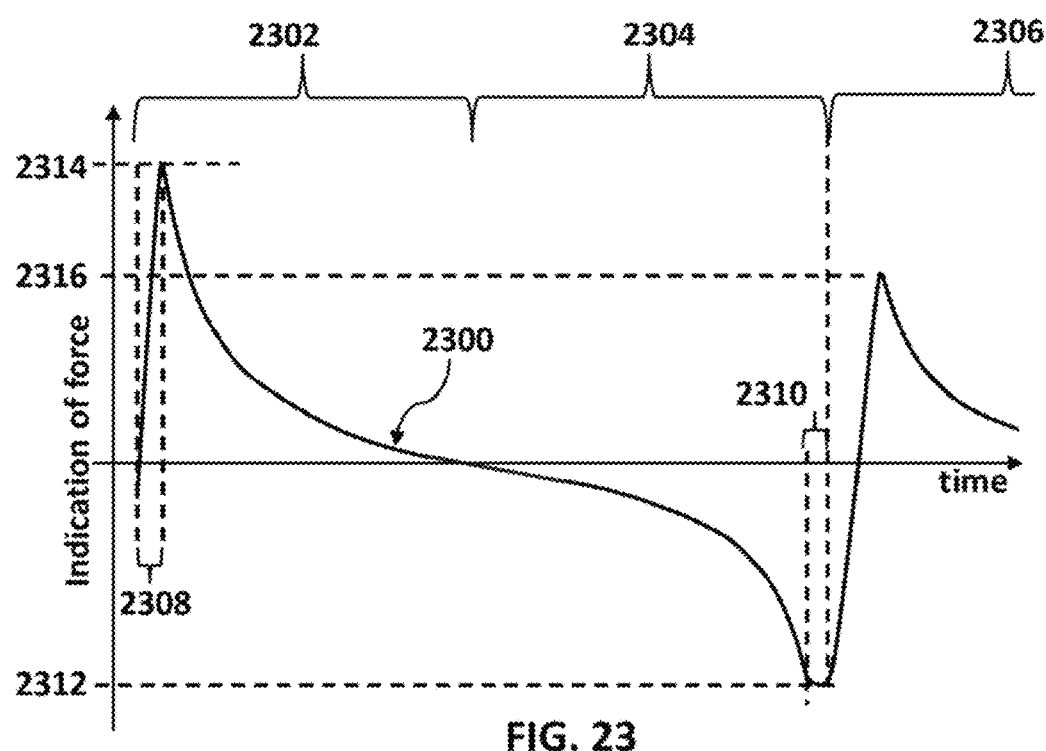
FIG. 23

ACCORDION MANEUVER WITH A BONE FIXATION DEVICE

RELATED APPLICATIONS

This application is a US Utility Patent Application, which claims the benefit of priority of under 35 USC § 119(e) of IL Patent Application No. 305408 filed 22 Aug. 2023, the contents of which are incorporated by reference as if fully set forth herein in its entirety.

TECHNOLOGICAL FIELD

The present disclosure, in some embodiments, thereof, relates to performing of accordion maneuver/s in bone treatment and, more particularly, but not exclusively, to performing of accordion maneuver/s in distraction osteogenesis treatment using a bone fixation device.

BACKGROUND ART

Background art includes; Makhdom A M, Cartaleanu A S, Rendon J S, Villemure I, Hamdy R C. The Accordion Maneuver: A Noninvasive Strategy for Absent or Delayed Callus Formation in Cases of Limb Lengthening. Adv Orthop. 2015; 2015:912790. doi: 10.1155/2015/912790. Epub 2015 Oct. 19. Which discloses "The distraction osteogenesis (DO) technique has been used worldwide to treat many orthopedic conditions. Although successful, absent or delayed callus formation in the distraction gap can lead to significant morbidities. An alternate cycle of distraction-compression (accordion maneuver) is one approach to accelerate bone regeneration. The primary aim of our study is to report our experience with the accordion maneuver during DO and to provide a detailed description of this technique, as performed in our center. The secondary aim is to present a review of the literature regarding the use of accordion maneuver. We reviewed the database of all patients undergoing limb lengthening from the year of 1997 to 2012. Four patients (6.15%) out of 65 showed poor bone regenerate in their tibiae and therefore accordion maneuver was applied for a mean of 6.75 weeks. Of these, three patients have had successful outcome with this technique. The literature showed that this technique is successful approach to trigger bone healing. However, details of how and when to apply this combination of distraction-compression forces were lacking. In conclusion, the accordion technique is safe noninvasive approach to promote bone formation, thus avoiding more invasive surgical procedures in cases of poor callus formation in limb lengthening."

Additional background art includes International Patent Application Publication No. WO2022024133A8, US Patent No. U.S. Ser. No. 11/076,801, US Patent Application Publication No. US20220346846, "Automated continuous distraction osteogenesis system for limb lengthening and reconstruction" to Yiyuan Fu et al, IPEM-Translation, Volume 5, 2023, 100016, ISSN 2667-2588, and "Novel approach to estimate distraction forces in distraction osteogenesis and application in the human lower leg" to Bachmeier et al, Journal of the Mechanical Behavior of Biomedical Materials, Volume 128, 2022, 105133, ISSN 1751-6161.

Acknowledgement of the above references, each of which is hereby incorporated by reference in its entirety, is not to be inferred as meaning that these are in any way relevant to the patentability of the presently disclosed subject matter.

GENERAL DESCRIPTION

Following is a non-exclusive list of some exemplary embodiments of the disclosure. The present disclosure also includes embodiments which include fewer than all the features in an example and embodiments using features from multiple examples, even if not listed below.

Example 1. A control system for use with an adjustable bone fixation device including a first fixation element and a second fixation element connectable to bone tissue portions either side of a treatment site;

the control system comprising:

one or more actuator configured to controllably adjust lengths of a plurality of adjustable length struts of the bone fixation device, the struts connecting said first and said second fixation elements of the bone fixation device, length adjustment thereof changing a spatial relationship between said first and said second fixation elements; and circuitry configured to control said one or more actuator to cause said first and second fixation element to perform an accordion maneuver by performing a plurality of actuations to adjust lengths of said adjustable length struts to create a reciprocal movement of said first and second fixation elements relative to each other.

Example 2. The control system according to Example 1, wherein said one or more actuator comprises a plurality of actuators, each actuator of said plurality of actuators configured to controllably adjust a length of a strut of said plurality of adjustable length struts.

Example 3. The control system according to Example 2, wherein said circuitry is configured to create said reciprocal movement by controlling at least two actuators of said plurality of actuators to simultaneously adjust length of at least two associated struts to move said first and said second fixation elements relative to each other.

Example 4. The control system according to any one of Examples 1-3, wherein said reciprocal movement of said first and second fixation elements is configured to provide a reciprocal movement to said bone tissue portions.

Example 5. The control system according to any one of Examples 1-4, wherein said circuitry is configured to:

i. receive a model including spatial relationships between said different portions of bone tissue and one or more portions of the adjustable fixation device; and control said plurality actuations to provide said reciprocal movement to said bone tissue portions, based on said spatial relationships.

Example 6. The control system according to Example 5, wherein said spatial relationships include spatial relationships between said bone tissue portions, said plurality of struts, and said first and said second fixation elements.

Example 7. The control system according to Example 6, wherein said first fixation element is configured to be anchored to bone tissue by at least two first rigid connectors extending from the fixation element into bone tissue, where said first fixation element and said at least two first rigid connectors are sized and shaped, and connection between said first fixation element and said at least two rigid connectors is such that said rigid first connectors extend into said bone tissue from different approach angles;

wherein said spatial relationships include a spatial relationships between said at least two first rigid connectors, said bone tissue, said plurality of struts, and said first and said second fixation elements.

Example 8. The control system according to any one of Examples 5-7, wherein planes of said first and said second fixation elements are orientated generally orthogonally to a central longitudinal axis of said bone tissue, wherein said circuitry is configured to control said one or more actuator to provide said accordion maneuver based on a spatial relationship between said first and said second fixation elements and said central longitudinal axis of said bone tissue.

Example 9. The control system according to Example 8, wherein said circuitry is configured to control said one or more actuator to provide said reciprocal motion in a direction generally parallel to said central longitudinal axis of said bone tissue.

Example 10. The control system according to any one of Examples 8-9, wherein said circuitry is configured to control said one or more actuator to provide said reciprocal motion which rotates said bone portions generally about said central longitudinal axis with respect to each other.

Example 11. The control system according to any one of Examples 1-10, wherein said reciprocal movement comprises oscillating movement of said first and second fixation elements relative to each other.

Example 12. The control system according to Example 11, wherein said oscillating movement of said accordion maneuver has a frequency of 0.01-10 Hz.

Example 13. The control system according to any one of Examples 1-12, wherein said plurality of actuations includes a repeating pattern of strut actuations, where repetition is at a frequency of 1-3 Hz to mimic physiological forces experienced by bone tissue during walking.

Example 14. The control system according to any one of Examples 1-13, wherein said accordion maneuver is performed a plurality of times, at a frequency of between 1 minute and 24 hours.

Example 15. The control system according to any one of Examples 1-14, wherein said plurality of actuations are such that said spatial relationship between said first and second fixation elements is the same prior to said plurality of actuations and after said plurality of actuations, which plurality of actuations maintaining said bone tissue in an initial position.

Example 16. The control system according to any one of Examples 1-15, wherein said reciprocal movement has an amplitude of 0.01 to 5 mm.

Example 17. The control system according to any one of Examples 1-16, wherein said plurality of actuations are such that said first and second fixation elements have:

an initial spatial relationship prior to said plurality of actuations; and a different end spatial relationship after said plurality of actuations;

wherein said plurality of actuations provide bone repositioning of said bone tissue.

Example 18. The control system according to any one of Examples 1-17, wherein at least one of plurality of actuations adjusts said spatial relationship to apply tensile force to bone tissue at a treatment site, wherein at least one of said plurality of actuations adjusts said spatial relationship to apply compressive force to said bone tissue at said treatment site.

Example 19. The control system according to any one of Examples 1-18, wherein said circuitry is configured:

to receive a bone positioning treatment plan comprising a plurality of intended bone positioning actuations associated with a plurality bone positioning times; and to actuate said at least one actuator according to said bone positioning treatment plan with one or more of said intended bone positioning actuations being configured to adjust said strut so as to change said spatial relationship thereby repositioning said bone tissue.

Example 20. The control system according to Example 19, wherein said circuitry is configured so that said intended bone positioning actuations are performed at different times to said plurality of actuations of said accordion maneuver.

Example 21. The control system according to any one of Examples 19-20, wherein an amplitude of an adjustment of the spatial relationship between the first and second fixation elements caused by said one or more bone positioning actuation is of 0.05 to 2 mm.

Example 22. The control system according to any one of Examples 19-21, wherein said control system comprises one or more sensor configured to generate one or more sensor signals indicative of a change associated with strut length dimension for one or more of said plurality of struts.

Example 23. The control system according to Example 22, wherein a first sensor signal of said one or more sensor signals is indicative of an axial force applied by a strut of said plurality of struts during one more of said plurality of actuations and/or one or more of said bone positioning actuations.

Example 24. The control system according to any one of Examples 22-23, wherein a second sensor signal of said one or more sensor signals is indicative of a change in dimension of said strut during one or more of said plurality of actuations and/or one or more of said bone positioning actuations.

Example 25. The control system according to any one of Examples 22-24, wherein said circuitry is configured to control one or more of said plurality of actuations and/or one or more of said bone positioning actuations based on said one or more sensor signals.

Example 26. The control system according to any one of Examples 22-25, wherein said circuitry is configured to determine one or more tissue feature, based on said one or more sensor signals.

Example 27. The control system according to Example 26, wherein said circuitry is configured to verify or adjust one or more of said plurality of actuations, based on one or more of:

said one or more sensor signals; and said one or more tissue feature.

Example 28. The control system according to any one of Examples 22-27, wherein said tissue feature is whether bone movement has occurred during an actuation.

Example 29. The control system according to any one of Examples 22-28, wherein said circuitry is configured to perform one or more of said plurality of actuations until said one or more sensor signals produced by said one or more sensor reaches a threshold value.

Example 30. The control system according to any one of Examples 22-29, wherein said one or more sensor comprises one or more of: a current sensor configured for monitoring current consumption of the actuator; a torque sensor; an encoder; and a load sensor.

Example 31. The control system according to Example 30, wherein said encoder is configured to measure distance and/or speed of movement of a moving part of said actuator, which moving part is configured to adjust said dimension of said adjustable strut.

Example 32. The control system according to any one of Examples 22-31, wherein said circuitry is configured to determine, from said one or more sensor signals: an amplitude of said strut dimension adjustment; and a speed of adjustment of said strut dimension.

Example 33. The control system according to any one of Examples 1-25, wherein said circuitry is configured to receive an actuation plan comprising:

said bone positioning treatment plan; and an accordion maneuver activation plan comprising actuation timing, direction, and amplitude for a plurality of sets of said plurality of actuations for performing said accordion maneuver a plurality of times, along with timing for performing each said accordion maneuver.

Example 34. A method of treatment comprising:

connecting a first fixation and a second fixation element of an adjustable bone fixation device to different portions of bone tissue, either side of a treatment site, the first and second fixation elements connected by a plurality of adjustable length rigid struts, adjustable by actuation of one or more actuator; and automatically actuating said one or more actuator a plurality of times to reciprocally adjust lengths of said plurality of adjustable length rigid struts to perform an accordion maneuver where said first and said second fixation elements move reciprocally relative to each other.

Example 35. The method according to Example 34, comprising:

receiving one or more measurement signals indicative of axial forces applied by said plurality of adjustable length rigid struts, during said automatically actuating; and determining one or more tissue parameter, based on said one or more measurement signals.

Example 36. The method according to Example 35, wherein said automatically actuating comprises performing a plurality of said accordion maneuvers over a time period;

wherein said receiving is for each of said plurality of accordion maneuvers; and wherein said determining said one or more tissue parameter is based on changes in said one or more measurement signals over said time period.

Example 37. The method according to any one of Examples 35-36, wherein said determining comprises evaluating said one or more measurement signals indicative of axial forces during a time associated with said actuation.

Example 38. The method according to any one of Examples 35-37, wherein said determining comprises:

receiving a three-dimensional (3D) model depicting spatial relationships between said different portions of bone tissue and one or more portions of the adjustable fixation device;

identifying, from the plurality of adjustable length struts, a strut most axially aligned with a treatment site on the bone based on the 3D model;

determining said one or more tissue parameter based on a measurement signal of said one or more measurement signals, which measurement signal is associated with said strut most axially aligned with said treatment site.

Example 39. The method according to Example 38, wherein said automatically actuating is only of said strut most axially aligned.

Example 40. The method according to any one of Examples 35-39, wherein said one or more tissue parameter comprises a measure of ossification of tissue at said treatment site.

Example 41. The method according to Example 40, comprising evaluating said measure of ossification; and generating an indication as to whether bone tissue is sufficiently health to:

initiate or resume bone repositioning; or remove the adjustable bone fixation device.

Example 42. The method according to any one of Examples 35-41, wherein said one or more tissue parameter comprises a level of confidence that an actuation performed during said automatically actuating resulted in a movement of bone tissue.

Example 43. The method according to any one of Examples 35-42, wherein said automatically actuating is verified or adjusted based on said one or more tissue parameter.

Example 44. A control system for use with an adjustable bone fixation device, the device having a frame connectable to bone tissue of a patient and at least one strut connecting to said frame;

the control system comprising:

at least one actuator associated with said at least one strut and configured to change a length of said at least one strut;

at least one sensor configured to generate a measurement signal indicative of axial force applied by said at least one strut; and circuitry configured to control said at least one actuator to:

activate said actuator to perform an actuation plan comprising a plurality of actuations each actuation changing a length of said at least one strut; and determine one or more tissue parameter, based on said measurement signal.

Example 45. The control system according to Example 44, wherein said circuitry is configured to control said at least one actuator based on said tissue parameter.

Example 46. The control system according to any one of Examples 44-45, wherein said circuitry is configured to verify and/or adjust an actuation of said plurality of actuations based on said tissue parameter.

Example 47. A control system for use with a bone fixation device connectable to bone tissue of a patient comprising:

an actuator configured to be coupled to said bone fixation device; and circuitry configured to:

signal said actuator to activate according to an activation plan including a plurality of actuations over time, where one or more of said plurality of actuations is associated with application of dynamization force to said bone tissue by one or more of:

applying vibrational forces to said bone fixation device; and controlling a rigidity of connection between said bone fixation device and said bone tissue of said patient.

Example 48. The control system according to Example 47, wherein said at least one actuator is configured to apply a force between a frame of said bone fixation device and one or more element connected to bone tissue of a subject.

Example 49. The control system according to any one of Examples 47-48, wherein said at least one actuator is disposed at a connection between a bone fixation element and a frame of said bone fixation device.

Example 50. The control system according to Example 49, wherein one or more of said plurality of actuations provides a movement of 0.5-5 mm repeating at a frequency of 5-50 Hz for a duration of 10 seconds-20 minutes.

Example 51. An adjustable bone fixation device comprising: the control system, the first fixation element, the second fixation element, and the plurality of adjustable length struts, according to any one of Examples 1-33; and wherein said first and said second fixation elements are sized and shaped to externally surround at least a third of a cross sectional circumference of said bone tissue, said cross section taken perpendicular to said central longitudinal axis.

Example 52. A control system for use with an adjustable bone fixation device, the device connectable to bone tissue of a patient and comprising a first fixation element and a second fixation element; the control system comprising: an actuator configured to adjust a spatial relationship between said first and said second fixation elements; and circuitry configured to control said actuator to cause the first and second fixation elements to perform an accordion maneuver by performing a plurality of actuations to create a reciprocal movement of the first and second fixation elements relative to each other.

Example 53. A method control of an adjustable bone fixation device, the device connectable to bone tissue of a patient and comprising a first fixation element and a second fixation element, where an actuator is configured to adjust a spatial relationship between said first and said second fixation elements, which method comprising: controlling said actuator to cause the first and second fixation elements to perform an accordion maneuver by performing a plurality of actuations to create a reciprocal movement of the first and second fixation elements relative to each other.

Example 54. A controller for use with a for use with an adjustable bone fixation device, the device connectable to bone tissue of a patient and comprising a first fixation element and a second fixation element, where an actuator an actuator is configured to adjust a spatial relationship between said first and said second fixation elements, which controller comprising: circuitry configured to control said actuator to cause the first and second fixation elements to perform an accordion maneuver by performing a plurality of actuations to create a reciprocal movement of the first and second fixation elements relative to each other.

Example 55. A method of operating a control system for use with a bone fixation device connectable to bone tissue of a patient, which method comprising: actuating at least one actuator configured to be coupled to said bone fixation device according to an activation plan including a plurality of actuations over time, where one or more of said plurality of actuations is associated with application of dynamization force to bone of a subject.

Example 56. A control system for use with an adjustable bone fixation device, the device connectable to bone tissue of a patient and comprising a first fixation element and a second fixation element; the control system comprising: an actuator configured to adjust a spatial relationship between said first and said second fixation elements; and circuitry configured to control said actuator to cause the first and second fixation elements to perform a plurality of actuations to create a reciprocal movement of the first and second fixation elements relative to each other.

Unless otherwise defined, all technical and/or scientific terms used within this document have meaning as commonly understood by one of ordinary skill in the art/s to which the present disclosure pertains. Methods and/or materials similar or equivalent to those described herein can be used in the practice and/or testing of embodiments of the present disclosure, and exemplary methods and/or materials are described below. Regarding exemplary embodiments described below, the materials, methods, and examples are illustrative and are not intended to be necessarily limiting.

Some embodiments of the present disclosure are embodied as a system, method, or computer program product. For example, some embodiments of the present disclosure may take the form of an entirely hardware embodiment, an entirely software embodiment (including firmware, resident software, micro code, etc.) or an embodiment combining software and hardware aspects that may all generally be referred to herein as a "circuit," "module" and/or "system."

Implementation of the method and/or system of some embodiments of the present disclosure can involve performing and/or completing selected tasks manually, automatically, or a combination thereof. According to actual instrumentation and/or equipment of some embodiments of the method and/or system of the present disclosure, several selected tasks could be implemented by hardware, by software or by firmware and/or by a combination thereof, e.g., using an operating system.

For example, hardware for performing selected tasks according to some embodiments of the present disclosure could be implemented as a chip or a circuit. As software, selected tasks according to some embodiments of the present disclosure could be implemented as a plurality of software instructions being executed by a computational device e.g., using any suitable operating system.

In some embodiments, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage e.g., for storing instructions and/or data. Optionally, a network connection is provided as well. User interface/s e.g., display/s and/or user input device/s are optionally provided.

Some embodiments of the present disclosure may be described below with reference to flowchart illustrations and/or block diagrams. For example illustrating exemplary methods and/or apparatus (systems) and/or and computer program products according to embodiments of the present disclosure. It will be understood that each step of the flowchart illustrations and/or block of the block diagrams, and/or combinations of steps in the flowchart illustrations and/or blocks in the block diagrams, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart steps and/or block diagram block or blocks.

These computer program instructions may also be stored in a computer readable medium that can direct a computer (e.g., in a memory, local and/or hosted at the cloud), other programmable data processing apparatus, or other devices to function in a particular manner, such that the instructions stored in the computer readable medium can be used to produce an article of manufacture including instructions which implement the function/act specified in the flowchart and/or block diagram block or blocks.

The computer program instructions may also be run by one or more computational device to cause a series of operational steps to be performed e.g., on the computational device, other programmable apparatus and/or other devices to produce a computer implemented process such that the instructions which execute provide processes for implementing the functions/acts specified in the flowchart and/or block diagram block or blocks.

Some of the methods described herein are generally designed only for use by a computer, and may not be feasible and/or practical for performing purely manually, by a human expert. A human expert who wanted to manually perform similar tasks, might be expected to use different methods, e.g., making use of expert knowledge and/or the pattern recognition capabilities of the human brain, potentially more efficient than manually going through the steps of the methods described herein.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIGS. 10C-16 are simplified schematics plot of strut length with time, according to some embodiments of the disclosure;

FIG. 17 is a method of bone treatment and/or diagnosis, according to some embodiments of the disclosure;

FIG. 18 is a method of performing an actuation plan, according to some embodiments of the disclosure;

FIG. 19 is a method of performing an actuation plan, according to some embodiments of the disclosure;

FIGS. 20A-B are a flowchart of a is a method of bone treatment, according to some embodiments of the disclosure;

FIG. 21 is a simplified schematic plot of strut length with time, according to some embodiments of the disclosure;

FIG. 22 is a simplified schematic plot of an indication of applied force with time, according to some embodiments of the disclosure; and FIG. 23 is a simplified schematic plot of an indication of applied force with time, according to some embodiments of the disclosure.

DETAILED DESCRIPTION OF EMBODIMENTS

Figure 1:
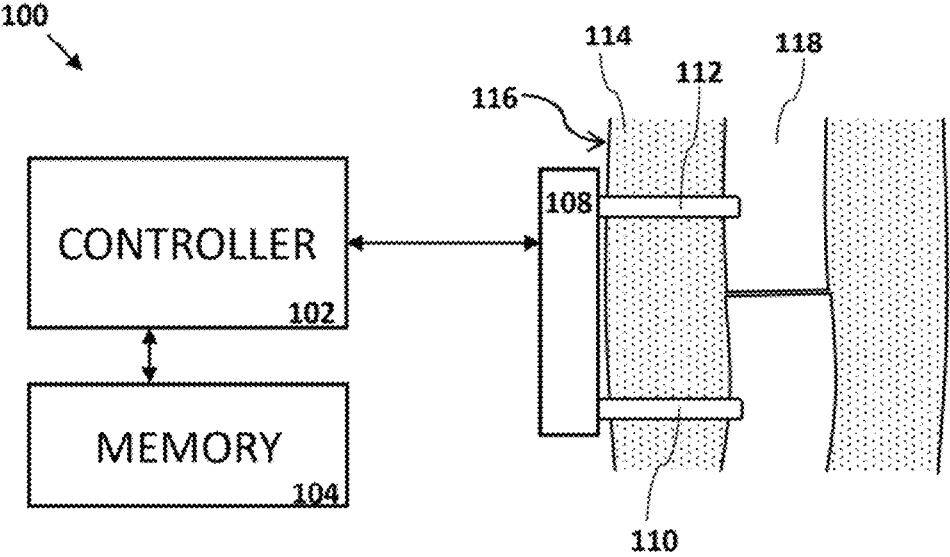
FIG. 1 illustrates a bone treatment system, according to some embodiments of the disclosure.

The present disclosure, in some embodiments, thereof, relates to performing of accordion maneuver/s in bone treatment and, more particularly, but not exclusively, to performing of accordion maneuver/s in distraction osteogenesis treatment using a bone fixation device.

Overview

A broad aspect of some embodiments of the disclosure relates to performing automated accordion maneuver/s on bone tissue. Where actuators configured to move bone tissue are controlled to reciprocally move bone tissue at one or more of selected times, frequencies, and amplitudes.

The accordion maneuver/s may be performed via a bone fixation device. Where the bone fixation device may include two or more fixation elements which are configured to be attached to bone tissue e.g., either side of a treatment site. Where, in some embodiments, the bone tissue is than of a limb (e.g., leg, arm). In some embodiments, the bone tissue is that of a jaw bone. In some embodiments, the bone tissue is spinal bone tissue.

One or more actuator connected to the fixation elements may be automatically controllable to change a spatial relationship between the fixation elements. Where the actuator may be configured to control a length of a strut (or more than one strut, optionally corresponding to more than one such actuator) connecting the two fixation elements. The accordion maneuver may be performed by automated control of the actuator/s to perform an accordion maneuver including a plurality of actuations to reciprocally move the fixation elements with respect to each other, for example, by reciprocally changing length of the strut/s connecting the two fixation elements.

The bone fixation device may also be used (e.g., in addition to being used to perform accordion maneuver/s) for bone positioning e.g., in a distraction osteogenesis (DO) treatment. Where repetitive changes (e.g., provided by the one or more actuator) to the spatial relationship between the fixation elements may change the spatial relationship between a first configuration to a second configuration in which bone tissue has a desired position.

An accordion maneuver may include at least two movements (e.g., an expansion of a distance between the fixation elements, followed by a contraction or vice versa). Where the at least two movements may occur during a short period of time e.g., in comparison to bone positioning movements which may occur at a lower frequency.

Accordion maneuver/s may be performed in a context of a bone repositioning treatment (e.g., DO). In some embodiments, a bone positioning treatment, may include a bone positioning phase followed by a tissue dynamization (also herein termed "dynamization" where tissue dynamization may include performance of accordion maneuver/s) phase in which accordion maneuver/s are performed. Alternatively or additionally, in some embodiments, tissue dynamization is performed prior to and/or during a bone positioning treatment where accordion maneuver actuation/s may occur prior to a start of repositioning of bone tissue and/or during bone positioning movements and/or interspersed with bone positioning movements of tissue.

The bone positioning phase of treatment may include repetitive movements of the fixation elements, spaced apart in time, to move relative position of bone portions.

The tissue dynamization phase (e.g., including accordion maneuver/s) may include repetitive movements of bone fixation elements (e.g., as provided by adjusting length of a strut connecting the fixation elements) where the position of bone tissue is not changed by the cumulative effect of the movements.

Accordion maneuver/s may be performed at different time periods to positioning of the bone tissue.

For example, bone portion/s may be is positioned in a desired position (e.g., over a number of weeks e.g., up to 90 days) and then accordion maneuver/s may be performed (e.g., to consolidate and/or strengthen new bone tissue formed during a distraction phase), for example, for up to 90 days.

Alternatively or additionally, a bone positioning treatment may include bone positioning and performance of accordion maneuver/s for bone dynamization occurring during a same time period, for example, during a same day.

The bone positioning movement/s and accordion maneuver/s may accompany each other e.g., separated by up to 30 minutes.

Alternatively, a plurality of temporally adjacent movements may provide both positioning and accordion maneuver/s.

In some embodiments, accordion maneuver/s may be used in response to progress of an initial DO treatment plan. Where the initial treatment plan may include accordion maneuver/s (e.g., for those with risk factor/s for slow bone growth e.g., diabetics, smokers) but where the progress may prompt additional accordion maneuver/s. Or where the initial treatment plan lacks accordion maneuver/s but where the progress may prompt incorporation of accordion maneuver/s into the bone positioning treatment.

For example, where, after an initial period of bone repositioning, bone repositioning is halted, and accordion maneuver/s are then performed. After performance of the accordion maneuver/s, bone repositioning may be resumed. Halting of repositioning and performing accordion maneuver/s may be implemented, after a diagnosis (e.g., of insufficient tissue growth) during a repositioning process (e.g., during DO). Potential benefits being avoidance of more invasive bone growth promoting treatment/s and/or increased speed of treatment.

An aspect of some embodiments of the disclosure relates to a control system comprising one or more actuator and a controller configured to instruct the one or more actuator to provide a plurality of actuations to perform accordion maneuver/s. The control system may be part of an adjustable bone fixation device and/or a controller for an adjustable bone fixation device, or may be a stand-alone device. Where a stand-alone (e.g., handheld) device hosting the control system may be configured for use with an adjustable bone fixation device.

An adjustable fixation device including the first and second fixation elements connected by one or more struts may be used for both positioning tissue (e.g., DO treatment) and performing accordion maneuver/s on tissue.

Optionally, both the positioning and the accordion maneuver/s may be performed by adjusting length of one or more of the struts. A potential advantage being the ability to perform both automated tissue (e.g., bone) positioning and automated accordion maneuver/s e.g., without manual adjustment to a device setup.

Strut length may be controlled by one or more actuator, for example, an actuator configured to control a length of each strut. Where actuator activation may be according to an actuation plan. The actuation plan including, for example, a plurality of actuations to supply accordion maneuver/s and actuation/s of a bone positioning treatment plan.

Control of actuations may include one or more of; control of timing of strut length change (e.g., for a plurality of struts) including a start and/or end time for the actuation, and/or control of a rate of strut length change and/or control of frequency of performance of repetitive actuations.

In an exemplary embodiment, control of bone positioning and/or accordion maneuver/s is implemented by a controller worn by a patient being treated, for example, the controller being physically connected (e.g., mounted) to a frame including the first and second fixation elements and/or directly attached to one or more of the first and second fixation elements. The controller may be connected to each of a plurality of actuators for example, the controller including data connections for transfer of control signals from the controller to the actuators.

Bone positioning and accordion maneuver/s may be implemented using a same controller and/or actuators. Alternatively or additionally accordion maneuver/s may be performed using a dedicated (e.g., separate controller) and/or actuator/s.

A broad aspect of some embodiments of the disclosure relates to one or both of bone positioning and dynamization (e.g., as provided by accordion maneuver/s) where sensor feedback is used in control of the bone positioning and/or accordion maneuver/s.

Control of activation of one or more actuator may include closed-loop control, where, for example, one or more measurement is used to determine and/or adjust one or more feature of one or more actuation.

Measurements may be used to verify and/or quantify bone movement (e.g., as produced by strut length actuation/s). For example, where an actuation plan includes desired bone movement and/or accordion maneuver/s, measurements are used to determine that the strut actuation achieves the desired bone movement and/or accordion maneuver/s.

Measurements may be used to provide feedback regarding a state of tissue of the patient. For example, where the measurements may be used to determine one or more tissue feature, e.g., density and/or quality of bone growth in a treatment region.

Where a measurement indicative of force applied to tissue (e.g., bone tissue) during an actuation may be used to control the actuation and/or future actuations.

Measurement of force, for example, provided by current consumption measurement/s for one or more actuator. Alternatively or additionally, measurement of force applied may be provided by one or more sensor e.g., a strain gauge. For example, one or more strain gauge at one or more bone fixation elements (e.g., transfixation pins) connecting the adjustable fixation device to bone tissue.

Measurement may be used to provide information regarding tissue (e.g., bone and/or soft tissue). For example, force measurement/s being used to diagnose a state of tissue and optionally thereby conclude and/or continue and/or adjust treatment.

For example, where force (e.g., tensile and/or compressive) is applied to position bone portions (e.g., to move the bone portions away from each other), a level of force applied may be used as an indication of a status of bone tissue and/or quality of bone growth e.g., between the bone portions.

Where a lower than expected tensile force (e.g., required to change a length one or more strut), may indicate a lack of bone growth and/or consolidation. Where an expected tensile force may indicate sufficient bone growth and/or consolidation. The level of tensile force may be used to verify and/or adjust an actuation (e.g., during the actuation) and/or to verify and/or adjust future actuations of an actuation plan. For example, where, upon identifying a higher than expected tensile force a rate of positioning may be increased. For example, where upon identifying a lower than expected tensile force, one or more feature of treatment may be reassessed by a medical practitioner, rate of bone positioning may be decreased, and accordion maneuver movements may be initiated and/or increased in magnitude and/or frequency.

In some embodiments, force measurements may be used to determine a start and/or end to treatment. For example, where accordion maneuvers applied prior to a bone positioning treatment and/or after completion of bone positioning may be used to determine whether tissue is sufficiently healed for initiation of bone positioning movements and removal of the adjustable fixation device, respectively. The measurements indicative of force applied to tissue may be used to control actuator/s to apply suitable force to bone tissue e.g., above force above a minimal level for accordion maneuver treatment e.g., force below a maximal level which causes pain and/or damage to bone tissue. In an exemplary embodiment, an accordion maneuver actuation includes changing a length of one or more strut until a measured threshold force is reached.

Alternatively or additionally to use of force measurements, measurement of strut length and/or change in position of bone portion/s may be used to control an actuation and/or future actuations.

Measurements indicative of force applied during accordion maneuver/s actuations and/or of strut length and/or bone position change/s may be saved for a plurality of subjects. Where, for example, the measurements (e.g., along with information regarding the treatment and/or subject) are used to determine and/or generate effective actuation plans e.g., for accordion maneuver/s actuations and/or bone positioning actuations. Where information regarding the treatment and/or subject may include HCP assessment of the subject and/or imaging based assessment. For example, bone density assessment using imaging e.g., x-ray.

Actuation for actuator/s of a device may be according to an actuation plan including one or more bone positioning actuation plan and one or more accordion maneuver/s actuation plan.

Bone positioning actuation plans may include one or more strut length changes where length change for each strut is in a single direction and/or where strut length changes incrementally in a same direction to change a strut length from an initial length an end length.

Accordion maneuver/s actuation plans may include a plurality of strut length changes where there is no net change in the strut length.

Actuation plans may include actuation timing, direction, and amplitude of actuations for one or more strut. Where timing may include one or more of frequency of performance of repetitive movements (e.g., for an accordion maneuver actuation plan, frequency of performance of reciprocal movements) and speed of individual movements.

In some embodiments, a treatment actuation plan may be considered to comprise of a bone positioning treatment plan and an accordion maneuver plan. Where actual movements of the fixation elements and/or strut/s may be determined as a combination of both plans. For example, each plan including fixation element position with time and/or strut actuations with time, e.g., the accordion movements being overlaid (added to) the bone fixation movements. When selecting and/or generating a treatment plan, features of a bone positioning plan may be selected and/or determined separately to those of an accordion maneuver plan.

An actuation plan may include one or more combined bone positioning and accordion maneuver/s actuation plan where a plurality of strut length changes including both contractions and expansions provide, after performance of the actuation plan, a net change in strut length and/or change in spatial relationship between first and second fixation elements.

An actuation plan may include rest periods of time where no actuations occur. The actuation plan may be adjusted according to feedback received during performance of the plan.

Although, within this document description includes description regarding strut length changes, bone position changes, and force applied to tissue, it should be understood the discussion may relate to associated activation of actuator/s e.g., to provide the described effect.

A broad aspect of some embodiments of the disclosure relates to active bone dynamization where repetitive forces and/or movements (e.g., accordion maneuver movements) are applied to a bone treatment site via controlled activation of one or more actuators.

In some embodiments, forces applied produce movement/s in bone tissue and/or change/s in spatial relationship between fixation elements connected to bone tissue. In some embodiments, force is not sufficient to move tissue, but a treatment and/or diagnostic force is applied to the tissue. Within this document, it should be understood that where movement is described in the context of accordion maneuver/s that, in some cases, forces are applied which do not produce movement in tissue.

The repetitive forces may be applied to the bone treatment site (e.g., to bone tissue itself) by actuation of actuator/s. Alternatively or additionally, movements may be a result of a controllable state (e.g., by one or more actuator) of a bone fixation device, where, for example, patient movements may generate the repetitive movements.

An aspect of some embodiments of the disclosure relates to automation of bone accordion maneuver/s where repetitive movements are applied to bone tissue via a bone fixation device connected to bone tissue.

For example, where the repetitive movements may be applied by automated control of actuation to apply movement/s to one or more portion of the bone fixation device.

For example, where the repetitive movements may be applied by automated control of length of one or more strut disposed between fixation elements attached to bone tissue. A bone treatment site (e.g., a position in which bone is divided to allow relative movement of the two parts of the bone) is typically located between two fixation elements. Strut length may be controlled by control of actuation of one or more actuator configured to change the length of the strut.

A plurality of struts attached to a frame including the two fixation elements may provide an ability to change a spatial orientation of the fixation elements to provide accordion maneuver/s in one or more direction, e.g., an axial with respect to the bone tissue and/or rotational direction/s. Where the axial accordion maneuver/s may apply tension and/or compression to the bone tissue. Where rotational accordion maneuver/s may apply torque to the bone treatment site.

Without wanting to be bound by theory it is theorized that repetitive movements of tissue (e.g., as applied by repetitive changes in length of one or more strut) stimulate tissue (e.g., bone) growth and/or dynamization (e.g., where growth increases density and/or strength of bone tissue).

Potential benefits of automating of dynamization include increased ease and/or accuracy of control of dynamization e.g., potentially enabling implementation of small and/or rapid and/or frequent dynamization actuations e.g., over time.

For example, by repetitive application of vibration to bone tissue. For example, by repetitive application of movements (e.g., compression and/or tension) between a bone fixation element and a frame of an adjustable bone fixation device. For example, by time period/s where the bone fixation device is in a dynamization configuration where patient movements apply the repetitive dynamization movements to the bone tissue.

For example, where a strut bone positioning length change is accompanied by a time period in which one or more of; the bone fixation device is in a dynamization configuration, movements are applied between bone fixation elements and the frame, and dynamization strut length changes are performed.

An aspect of some embodiments of the disclosure relates to automated actuation of a bone positioning actuation plan and/or an accordion maneuver actuation plan having feature/s which change with time.

For example, a magnitude of movements may change during a time duration of a treatment. For example, the magnitude increasing with time or decreasing with time and/or changing e.g., based on feedback. Where the magnitude may be of, for example, strut extension/s and/or relative change in position between the first and second fixation elements.

For example, a frequency of movements may change during treatment: More frequent bone positioning and/or accordion movements may be actuated at one or more portion of a treatment than at other portion/s of the treatment. Where, in some embodiments, frequency of one or both kinds of movement is adjusted and/or verified using feedback measurements.

An aspect of some embodiments of the disclosure relates to an accordion maneuver actuation plan including movements which mimic physiological forces experienced by bone tissue during normal body movement/s e.g., during walking.

Where, in some embodiments, for one or more period of time (e.g., simulated walking periods of time) forces and/or movements applied by the actuator/s are repetitive and/or cyclical.

In some embodiments, repetition of actuations to simulate walking forces is at frequency/s of steps and/or paces of normal walking. For example, where walking force actuations and/or patterns of actuations repeat at a frequency of 0.5-5 Hz, or at 1-3 Hz, or lower or higher or intermediate frequencies or ranges.

In some embodiments, walking forces are simulated by strut movements and/or fixation element movements including at back and forth movements. Where an amplitude of the strut and/or fixation element movements may be of 0.5 mm (e.g., 0.5 mm compression and extension). The strut and/or fixation element movements may be applied 5-200 times, or 50-200 times, or about 100 times a day, or lower or higher or intermediate numbers of repetitions or ranges.

In some embodiments, a walking forces are simulated by a compression (foot to ground, push off) followed by a release e.g., the compression simulating foot impact and push off from the ground, and the release simulating time the foot passes through the air prior to the next step.

In some embodiments, actuations simulating contact of the foot with the ground may have varying compressions e.g., to simulate a heel strike followed by toe push off.

In some embodiments, joint movement (cycling a knee or ankle joint around its axis) is simulated by a compression and release pattern of a plurality of struts around the bone tissue.

An aspect of some embodiments of the disclosure relates to using spatial relationship/s between bone tissue and the adjustable fixation device to determine actuation/s and/or actuation plan/s e.g., for different purposes. In some embodiments, a model (e.g., 3D model) including spatial relationship/s between bone tissue and the adjustable fixation device is used to generate an accordion maneuver actuation plan and/or diagnostic actuation/s. In some embodiments, the model includes spatial relationship/s for different times within a treatment. In some embodiments, a known position of bone tissue with respect to portion/s of the adjustable fixation element may be used to select individual strut actuation/s. For example, in an exemplary embodiment, bone tissue is evaluated by actuating a strut most axially aligned with a longitudinal axis of the bone e.g., when evaluating if bone is sufficiently healed for removal of the adjustable fixation device. Where strut spatial orientation with respect to an orientation of a bone longitudinal axis, in some embodiments, is received in and/or determined using the model. In some embodiments, a subset of struts of the device most aligned with the longitudinal axis of the bone are used.

An aspect of some embodiments of the disclosure relates to using accordion movements to correct for positioning error e.g., accumulated positioning errors. In some embodiments, discrepancy between desired strut and/or bone movement and actual active movements are determined. Where, in some embodiments, based on determined discrepancy/ies, actuations may be adjusted. The adjustments may be performed, for example, for positioning error associated with one or more bone positioning movement, during accordion maneuvers, e.g., where a net increase or decrease in strut length for one or more strut is implemented during the accordion maneuver to compensate for the positioning error (at least partially). In some embodiments, actuator sensors include encoders configured to measure strut extension and/or contraction. Where, for example, discrepancy between encoder measurements and expected encoder measurements according to control signals sent to actuators may be used to determine positioning error which may then be compensated for in subsequent strut movements e.g., bone positioning and/or accordion maneuver movements.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

FIG. 1 illustrates a bone treatment system 100, according to some embodiments of the disclosure.

System 100 may include one or more bone fixation element 110, 112 configured to be attached to bone tissue 114. For example where bone fixation element/s 110, 112 include or are attached to one or more of pin/s (e.g., transfixation pins), rods, wires (e.g., k-wires) which are connected to bone tissue 114. Bone fixation element/s 110, 112 may extend outwards from bone tissue towards an outer skin surface 116.

Accordion maneuver/s stimulation may be applied to bone tissue via bone fixation elements 110, 112. Where accordion maneuver stimulation may be applied by actuation of one or more actuator 108. Actuator/s 108 may be controlled by a controller 102. Where controller 102 may instruct actuator actuation/s for one or both of bone positioning and to provide accordion maneuver/s. For example, according to an actuation plan e.g., as described in more detail elsewhere in this document.

Actuator/s 108 may be configured themselves to apply stimulation to bone tissue 114 via bone fixation element/s 110, 112.

Alternatively or additionally, actuator/s 108 may be configured to change a configuration of system 100, to initiate and/or allow and/or enable accordion maneuver/s stimulation.

Figure 2:
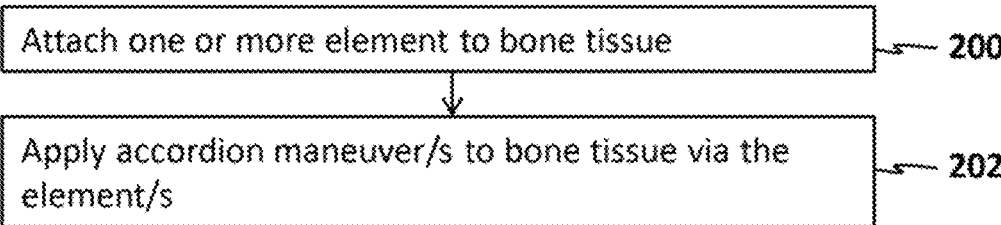
FIG. 2 is a method of bone treatment, according to some embodiments of the disclosure.

FIG. 2 is a method of bone treatment, according to some embodiments of the disclosure.

At 200, bone fixation element/s may be attached to bone tissue. For example during a surgical procedure where bone tissue may be cut to allow movement of bone portions relative to each other either side of the cut.

At 202, active dynamization forces are applied to bone tissue via the bone fixation elements. For example, by application of accordion maneuver/s to bone tissue.

Where the dynamization stimulation may be mechanical. For example, including application of one or more of vibration, tensile force, compressive force, and torque on the bone tissue.

Dynamization stimulation may be actively applied, for example, by one or more actuator operating on the bone fixation element/s directly, and/or indirectly e.g., through one or more additional elements. For example where the dynamization stimulation includes accordion maneuver/s performed by adjustment of dimension (e.g., length) of one or more strut connecting the fixation elements.

Alternatively or additionally, dynamization simulation is activated by one or more actuator, but the stimulation itself is associated with movements of the subject. For example, as described regarding adjustable connectors 306, 308 FIG. 3.

For example, where in a first configuration a frame is connected (e.g., rigidly connected) to bone fixation element/s and where active dynamization may be applied by reducing a level of attachment of one or more fixation element to the frame and/or controlling the level of attachment. Where the active dynamization forces may be generated by movements of the patient. For example during walking.

Patient movements during the dynamization configuration may be prescribed as part of a treatment. Where, for example, a patient may be instructed (e.g., via a user interface of the system) to perform particular movements to provide the dynamization forces.

Figure 3:
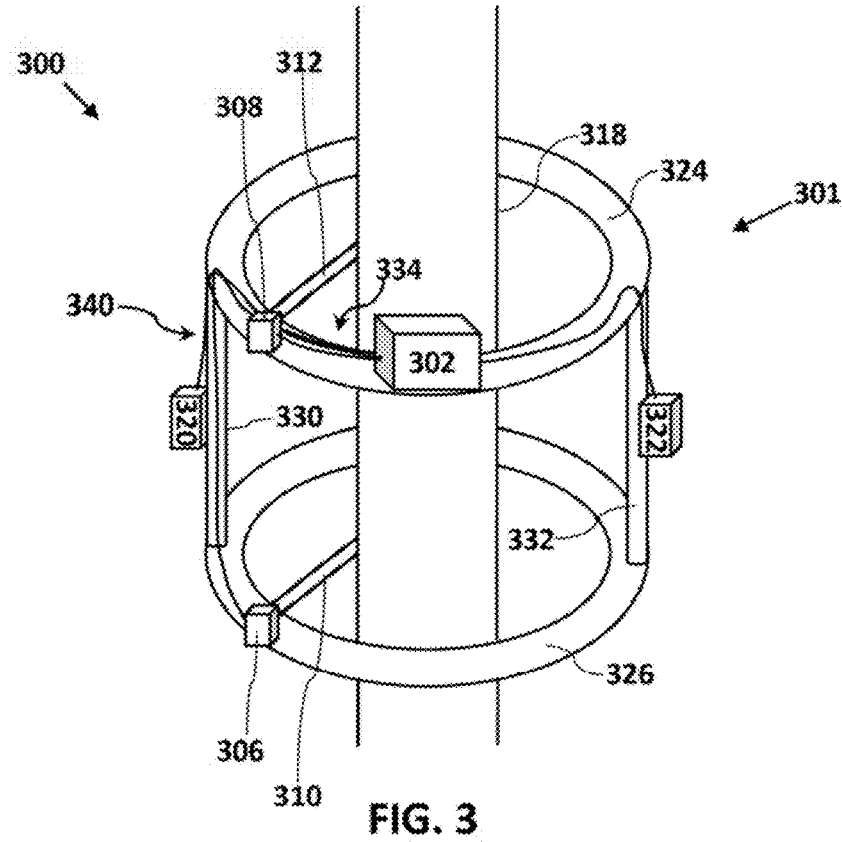
FIG. 3 is a simplified schematic of a bone treatment system, according to some embodiments of the disclosure.

FIG. 3 is a simplified schematic of a bone treatment system 300, according to some embodiments of the disclosure.

System 300 may include an adjustable bone fixation system 301 including a controller 302, one or more bone fixation elements 310, 312, and one or more actuators 306, 308, each of which may include one or more feature of a corresponding element (controller 102, one or more bone fixation elements 110, 112, and one or more actuators 106, 108 respectively) of system 100 FIG. 1.

System 300 may include a frame to which bone fixation elements 310, 312 are attached e.g., external to a body surface of the patient. Bone fixation elements 310, 312 may be fixed to bone tissue 318. The frame may include a first fixation element 324 and a second fixation element 326. Where one or more strut 330, 332 may connect fixation elements 324, 326.

Figure 5A:
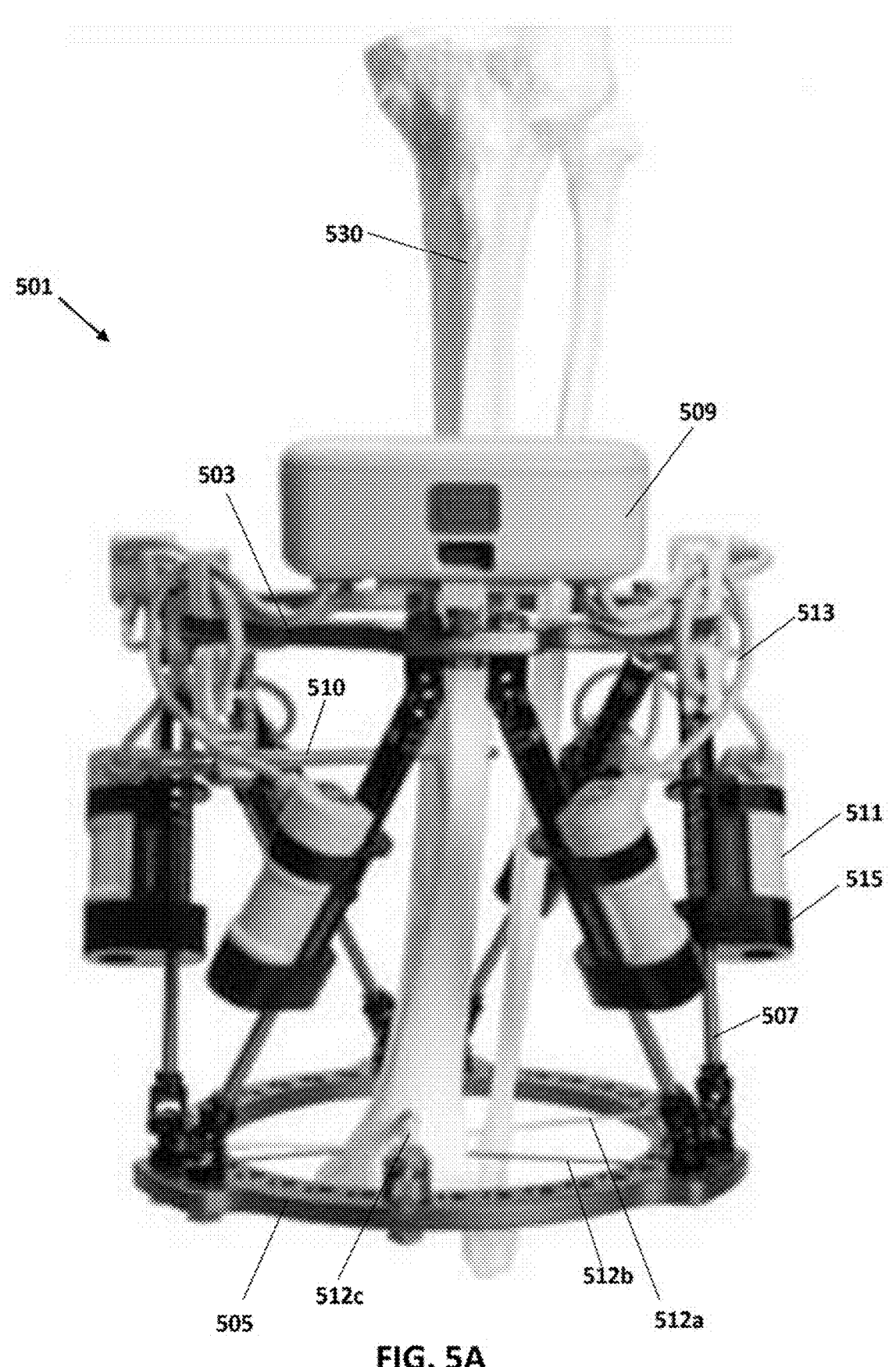
FIG. 5A illustrates an adjustable bone fixation device connected to a bone, according to embodiments of the presently disclosed subject matter.

The frame and struts 330, 332 may be part of an adjustable bone fixation device 301 which, for example, includes one or more feature of bone fixation device 501 FIG. 5A. Where length of strut/s 330, 332 may be adjusted to change a distance between first and second fixation elements 324, 326, for example, in order to reposition bone portion/s. Adjustment of strut length may be performed by activation of one or more actuators 320, 322, for example, for each strut by an associated actuator (e.g., strut 330 by actuator 320, strut 332 by actuator 322). Control of actuators e.g., according to an actuation plan, may be effected by controller 302. Controller 302, may be connected wirelessly and/or via data and/or power cables 334 to actuators 320, 322.

Dynamization may be performed by one or more of; length adjustment of the strut/s 330, 332, application of forces to one or more portion of the frame and/or bone fixation elements, and changing a configuration of the system.

Application of forces to the frame and/or bone fixation elements may be by activation of one or more dedicated dynamization actuator 306, 308. Dynamization actuators 306, 308 being different from actuators 320, 322 configured to adjust strut length. Dynamization actuators 320, 322 may themselves apply dynamization forces, for example, actuator/s 306, 308 may vibrate.

Where the vibration of actuator/s 306, 308 may cause repetitive movement of one or both of bone fixation elements 310, 312, and/or a spatial relationship between element/s 310, 312 (e.g., between fixation elements 324, 326). Where the repetitive movements may have one or more of: an amplitude of 0.1-5 mm, or 0.5-5 mm, movements occurring at a frequency 5-50 Hz, and for a duration of 10 seconds-20 minutes.

Vibration actuator/s may be implemented with one or more of a solenoid movement mechanism, excentre mechanism, and piezo actuator/s. Where amplitude of the vibration movements may be pre-set, the controller providing control signals to control frequency and/or the duration of the vibrational movements.

Alternatively or additionally to direct application of forces, dynamization actuator/s 320, 322 may be configured to change a configuration of system 300, for example, by changing a configuration of connection between bone fixation element/s 310, 312 and one or more portion of the frame e.g., fixation elements 324, 326 respectively. For example, by loosening and/or increasing an elasticity and/or increasing a rigidity of connection between the frame and one or more bone fixation element 310, 312.

Control of dynamization actuators 306, 308 may be via controller 302 which may control both strut adjustment actuators 320, 322 and dynamization actuators 306, 308. For example, each according to an activation actuation plan e.g., a bone positioning actuation plan and a dynamization actuation plan, respectively. Controller 302 may be connected wirelessly and/or by power and/or data cables 340 to dynamization actuator/s 306, 308.

Figure 4:
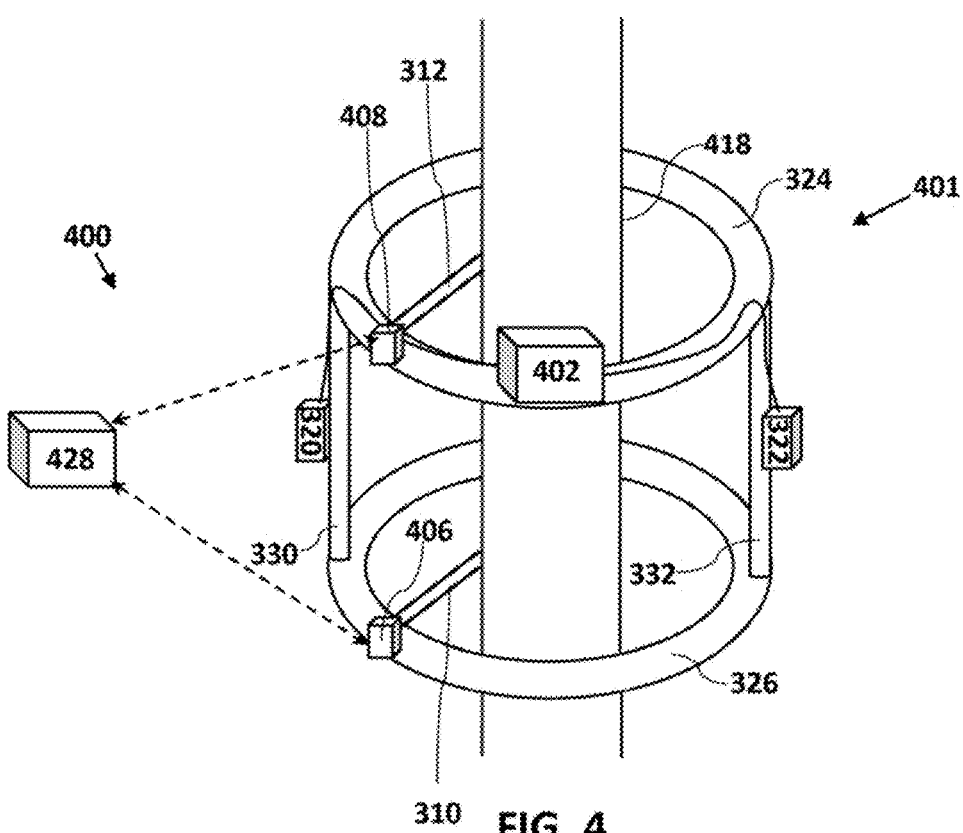
FIG. 4 is a simplified schematic of bone treatment system, according to some embodiments of the disclosure.

FIG. 4 is a simplified schematic of a bone treatment system 400, according to some embodiments of the disclosure.

Bone dynamization system 400 may be separate to an adjustable bone fixation device system: Where an adjustable bone fixation system 401 may include one or more feature of bone fixation device 301 FIG. 3, including one or more bone fixation elements 310, 312, fixation elements 324, 326 connected by struts 330, 332, where strut adjustment is controlled by a control system including a controller 302 and one or more strut actuators 320, 322.

Bone dynamization system 400 may include a controller 428 and one or more dynamization actuators 406, 408. Where dynamization actuators 406, 408 may include one or more feature of dynamization actuator/s 306, 308 FIG. 3.

Where, for example, controller 402 controls bone positioning via strut adjustment and controller 428 controls application of forces for bone dynamization.

In some embodiments, controllers 402, 428 are time synchronized e.g., via data connection therebetween and/or via connection to external circuitry. For example, where combined data regarding actuation plans (bone positioning and bone dynamization) is used in completion of the actuation plans. For example, to prevent bone positioning movements occurring at a same time as dynamization is enabled. Bone dynamization system 400 may be separable from bone adjustment system 401. For example, removable from system 401 for use with another system. For example, where bone dynamization system 400 may be used with an adjustable bone fixation device where bone positioning is performed manually. Dynamization actuation plan/s being for example generated using details of the manual positioning actuation plan. Optionally, system 400 includes one or more user interface where the user interface may instruct a user (e.g., the patient) to perform manual adjustments, for example, system 400 automatically implementing dynamization actuation plan/s.

Bone dynamization system 400 may include a controller for each actuator of the system. Where one or more dynamization units each including one or more actuator and a controller may be used e.g., in conjunction with bone positioning system 401. In some embodiments, a dynamization unit (e.g., hand-held) is coupled to an adjustable bone fixation device periodically (optionally in different positions) for performance of dynamization movements. A single dynamization unit, for example, being used in treatment of more than one subject during an overlapping treatment time period.

In some embodiments, actuators 406, 408, are controlled (e.g., according to an actuation plan) to perform repetitive actuations to apply repetitive dynamization movements (and/or forces) to bone tissue via bone fixation elements 310, 312. For example, where, in some embodiments, actuator/s 310, 312 act to expand and/or contract a space between a fixation element 324, 326 and bone fixation element/s 310, 312.

In some embodiments, element/s 406, 408 include adjustable connectors, where actuator/s (e.g., of the dynamization controller 428 and/or of the element/s themselves) are configured to adjust a state of the connector/s, for example, increasing flexibility and/or elasticity of the connection to enable dynamization e.g., via patient movements.

Optionally, the connectors 406, 408 may include suspension device/s and/or shock absorbers.

One or more dynamization devices may be physically coupled to the bone fixation device for implementation of automated dynamization. For example, during a treatment time period. For example, periodically, during a treatment time period.

Alternatively, or additionally, one or more dynamization controller may have a data connection to actuator/s of the dynamization system for control of dynamization.

System 400 may include more than one controller 402, 428. A first controller 402 configured to control actuation of strut adjustment actuators 320, 322 and a second controller 428 configured to control actuation of dynamization actuators 406, 408. Where second controller 428 may be physically attached to the frame and/or to a strut or may be separate.

FIG. 5A illustrates an adjustable bone fixation device connected to a bone, according to embodiments of the presently disclosed subject matter.

FIG. 5A may illustrate feature/s of one or more of the bone fixation devices illustrated in FIG. 1, FIG. 3, and FIG. 4.

Bone fixation device 501 is generally intended to be connected to the bone of a patient, in a surgical process. In some cases, the device is used for the treatment of a fractured bone, misaligned bone(s), a deformed bone, a bone that needs to be changed in length, and/or other orthopedic or generally bone related conditions.

The bone fixation device is generally comprised of a frame constituting of at least two portions, 503 and 505, and a plurality of struts 507 (e.g., 1, 2, 4, 5, or 6 or intermediate or larger number of struts), connecting the at least two portions of the frame. In an exemplary embodiment, 6 struts 507 connect two portions of the frame, the 6 struts providing, potentially, the ability to control 3D spatial relationship between two frame portions. In some embodiments, as shown, the bone fixation device is shaped as a hexapod, and the two frame portions are formed as two rings having six struts which interconnect the rings. In other embodiments, the two frame portions may include open rings, arc shaped frames, rods, and/or otherwise shaped frame portions. In some embodiments, each frame portion encompasses and/or surrounds a cross sectional (with respect to a limb and/or bone central longitudinal axis) circumference of the limb and/or bone tissue. For example, by at least a third, or half, or a majority of the limb and/or bone circumference.

In some embodiments, the two portions of the frame are at least partially connected to the bone via pins (e.g., transfixation pins), rods, wires (e.g., k-wires), or other suitable fixation elements 510, 512*a*, 512*b*, 512*c* which extend from the frame portion and into the bone. Adjustment of the struts, such as by lengthening or shortening a strut along a linear axis, modifies the distance between the two frame portions (e.g., by pulling on the frame portions towards each other or by pushing the frame portions away from each other). In an example, shortening of struts can approximate the two frame portions towards each other; lengthening of struts can distance the two frame portions away from each other. Adjustment of the struts can also modify the relative position and/or orientation of the two frame portions (and the bone portions to which the frame portions are attached) with respect to each other, for example, shortening of some of the struts and/or lengthening of some of the struts can change an angular orientation of the frame portions with respect to each other (for example, when the frame portions consist of rings, change the plane in which the ring lies and/or change a rotational positioning of the ring).

Automated adjustment of the bone fixation device is carried out, in accordance with some embodiments, by a control system which is operably connected to the device. The control system is generally comprised of a control unit 509 and a plurality of actuators 511, such as motors (e.g., linear motors). In some embodiments, each of the actuators is associated with a single strut and is configured to drive the adjustment of the specific strut. In some embodiments, the control unit is electrically connected to the actuators via cables 513. (Additionally or alternatively, a wireless connection may be established between the control unit and the actuators).

In some embodiments, each of the actuators is maintained within a designated adaptor 515 which holds the actuator in an operable coupling with the strut. In some embodiments, the adaptor is shaped to maintain the actuator axially aligned with the strut which the actuator adjusts. Alternatively, in some embodiments, an actuator may be contained (e.g., embedded) within the strut itself.

In some embodiments, the control system of the bone fixation device comprises one or more sensors, for example: sensors configured for obtaining system related measurements, such as for measuring operational parameters of the actuators (e.g., torque generated by an actuator, current consumption, operation voltage, rotation speed of the actuator, etc.); and/or sensors configured for obtaining measurements related to the surroundings, such as for measuring environmental conditions (e.g., temperature, humidity), measuring a load or impact on the device, measuring a posture of the patient, etc. For example, a sensor for measuring load acting on the device, may be positioned, for example, at an attachment area of a strut to the top frame portion.

It is noted that while a hexapod external fixation device is shown herein, other bone fixation devices such as a monorail are also contemplated.

Figure 5B:
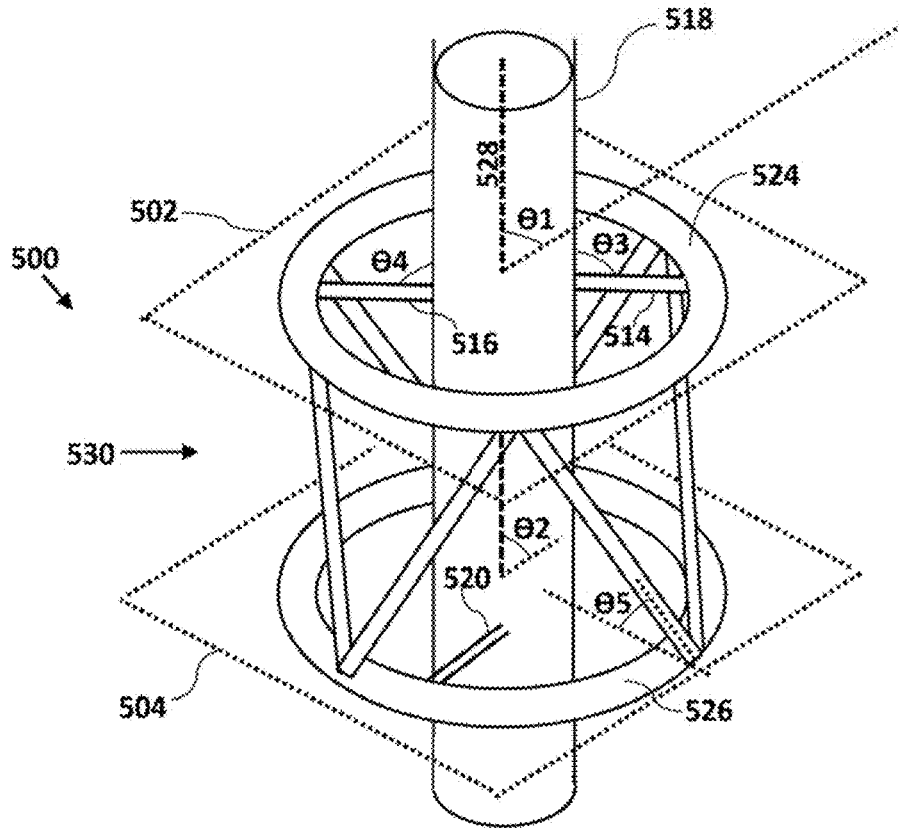
FIG. 5B illustrates an adjustable bone fixation device connected to a bone, according to embodiments of the presently disclosed subject matter.

FIG. 5B illustrates an adjustable bone fixation device 500 connected to a bone 518, according to embodiments of the presently disclosed subject matter.

In some embodiments, FIG. 5B is a simplified schematic of portion/s of FIG. 5A. For simplicity, actuators and a controller are not illustrated, but it should be understood that, in some embodiments, such component/s are included, for example, as described in FIG. 5A and/or FIG. 3 and/or FIG. 4.

FIG. 5B illustrates planes 502, 504 of orientation of first and second fixation elements 524, 526 (e.g., corresponding to frame portions 503, 505 FIG. 5A). Where planes 502, 504 may be representative of (e.g., contacting) a surface of fixation elements 524, 526 and/or a general orientation of the fixation elements with respect to bone tissue 518 and/or other portion/s of device 500.

In some embodiments, fixation elements 524, 526 are generally orientated orthogonally to longitudinal axis 528 (e.g., central longitudinal axis) of bone tissue 518. Where, for example, one or both of planes 502, 504 are orthogonal to (or one or both of angles θ1, θ2 between the planes and axis 528) are within 10 or 20 degrees of orthogonal to) axis 528.

In some embodiments, a plurality of bone fixation elements 514, 516, 520 (also herein termed "connectors") connect bone tissue 518 to device 500. In some embodiments, at least two bone fixation elements extend into bone tissue 518 from different directions, and/or at different angles θ3, θ4, θ5 and/or different circumferential regions of the bone tissue. Where, in some embodiments, at least two bone fixation elements 514, 516 connect a single fixation element 524 to bone tissue 518 from different directions θ3, θ4. Where, in some embodiments, a first bone fixation element 514 connects first fixation element to bone tissue in a first direction and a second bone fixation element 520 to bone tissue in a second direction, where the first and second directions are different.

Directions of connectors may be understood in terms of vector direction of an axis of the connector from the fixation element to the bone tissue. For example, opposite directions (e.g., illustrated by connectors 514, 516) where the bone fixation elements extend into bone tissue from opposite sides of the bone.

In some embodiments, at least two bone fixation elements 514, 516 and/or 514, 516 extend from different circumferential portions of a single fixation element 524.

Although illustrated as extending parallel and/or within planes 502, 504, one or more connector may extend into tissue at an angle to a plane of the fixation element which they are connected to.

In some embodiments, one or more of a plurality of struts 530 connecting fixation elements 524, 526 are angled (e.g., not orthogonal to, e.g., at an angle of less than 90 degrees to) with respect to planes 502, 504. Where, in some embodiments, circumferentially adjacent struts may connect to a fixation element at a same general location and may connect to the opposing fixation element with a separation between the adjacent struts. In some embodiments, struts 530 may be arranged to form a repeating triangulation pattern between the two fixation elements e.g., as illustrated in FIG. 5A. Where, in some embodiments, angles e.g., angle θ5 of the struts with respect to the planes of the fixation elements may be defined by distance between the fixation elements and the diameter and/or extent orthogonal to axis 518 of the fixation elements.

Figure 6A:
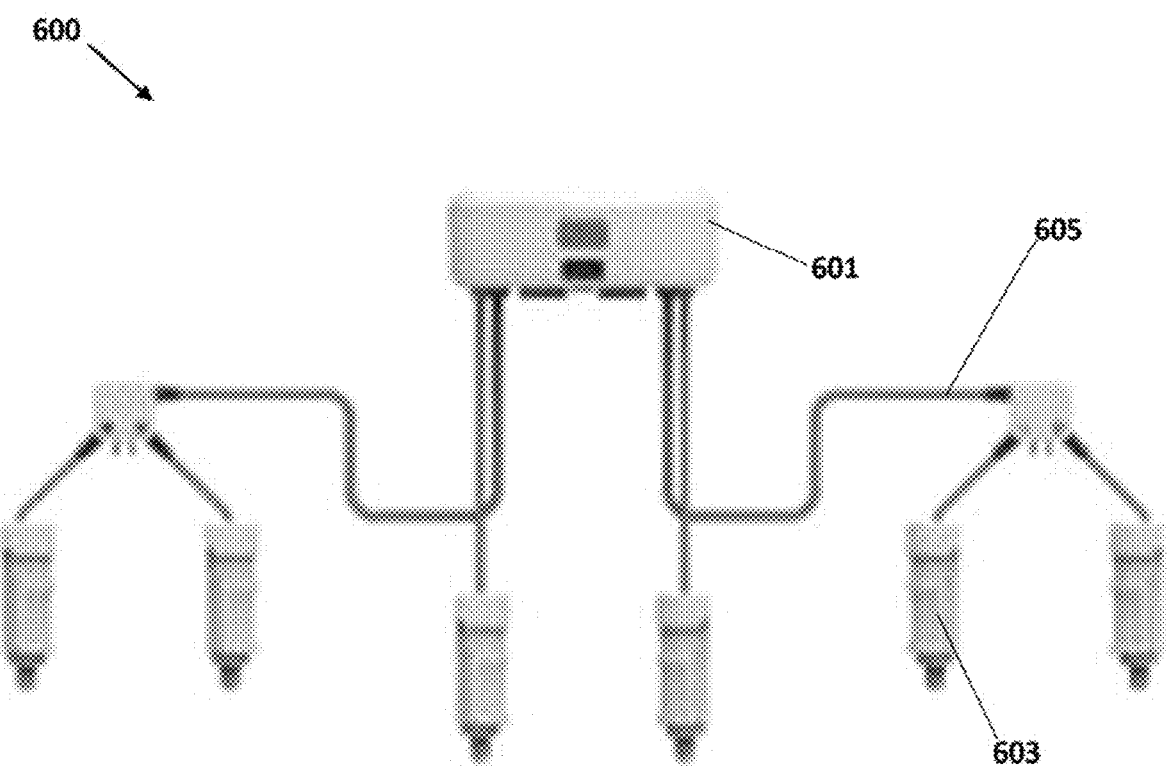
FIG. 6A illustrates a control system for use with an adjustable bone fixation device, according to embodiments of the presently disclosed subject matter.

FIG. 6A illustrates a control system for use with an adjustable bone fixation device, according to embodiments of the presently disclosed subject matter.

A control system 600 as shown generally comprises a control unit 601, comprising a housing in which computational, processing, communication and/or memory means are contained. The control unit is operably connected to a plurality of actuators 603, optionally, via cables 605 or other suitable wiring. In some embodiments, each of the actuators is comprised of a motor, for example, a brush DC motor or a brushless DC motor.

In some embodiments, control unit 601 comprises a power source (not shown), for example an electric power source. In some embodiments, the power source comprises a battery, for example a non-replaceable battery or a replaceable battery or a rechargeable battery. In some embodiments, the control unit delivers electric power from the power source to each of the actuators via the cables. Optionally, the battery is sufficient to power the device for as long as the bone fixation device is required to stay connected to the bone, for example, for a time period of between 1 week-6 months, or 1-6 months, or 1-3 months, or lower or higher or intermediate durations or ranges.

In some embodiments, in use, the control system is coupled to the frame and the struts of the bone fixation device. In some embodiments, each actuator is operably connected to a strut such that activation of the actuator generates torque for adjusting the strut. In an example, the actuator rotates a gear or a gear train which is operably coupled at its end to a threaded lead screw. Movement of the lead screw linearly shortens or lengthens the strut by extending or contracting an adjustable segment of the strut. It is noted that other mechanisms may be used for adjusting the strut, for example, a hydraulic mechanism, a spring-based mechanism, a magnetic mechanism, and/or other mechanism suitable for extending or contracting an adjustable segment of the strut.

Accordion maneuver/s may be performed where the lead screw provides linear shortening and lengthening of the strut. For example, where the lead screw is turned in one direction and then the other to provide reciprocal moment of the accordion maneuver. Where the turning of the lead screw may be associated with actuator rotation. Where desired accordion maneuver features e.g., including one or more of amplitudes of the movements, speed of the movements, and frequency of the movements may be controlled by turning of the lead screw.

In embodiments in which the actuator is external to the strut, the actuator may be held by an adaptor or other suitable restraining means for coupling the actuator to the struts. In embodiments in which the actuator is embedded within the strut, a connector may be used for connecting the control unit (such as via the cables or other wiring) to the embedded actuator.

In some embodiments, the control unit housing is removably connected to the frame, for example via fasteners.

In some embodiments, an actuation plan is uploaded (or otherwise communicated) to the control unit, in which it can be stored (for example, in a memory of the control unit). Optionally, an actuation plan is communicated to the control unit over the network.

The actuation plan is designed to carry out a treatment regimen, which can be determined based on a diagnosis of the patient (for example, using the results of tissue imaging); based on patient parameters (e.g., age, level of physical activity); based on the required bone modification; and/or other factors.

In some embodiments, the actuation plan sets parameters according to which the control system operates the actuators. The parameters can be set for each actuator separately, or for multiple actuators together. The parameters can be set per a single actuation session, or per multiple actuation sessions together.

Operational parameters set by the actuation plan can include, for example:

Timing of actuation (e.g., an actuation schedule, time intervals (or permitted ranges) between actuation sessions, specific times (or permitted ranges) for initiating and/or for completing an actuation session, a total time period over which device adjustment should be performed (e.g., 1 day, 1 week, 6 weeks, 1 month, 3 months), and/or other time related parameters);

An actuation session duration or a permitted range thereof;

A torque range or limit to be generated by an actuator; and/or other operational parameters of the actuator which affect, directly or indirectly, the axial adjustment of the strut, such as: current consumption of the actuator, voltage, rotation speed of the actuator, or other.

A desired change in the length of a strut or a permitted range thereof, for example, a length measured along the strut between the end attachments of the strut to the two portions of the frame.

A travel range of a strut, for example, a total distance along which the strut is planned to be adjusted.

Figure 6B:
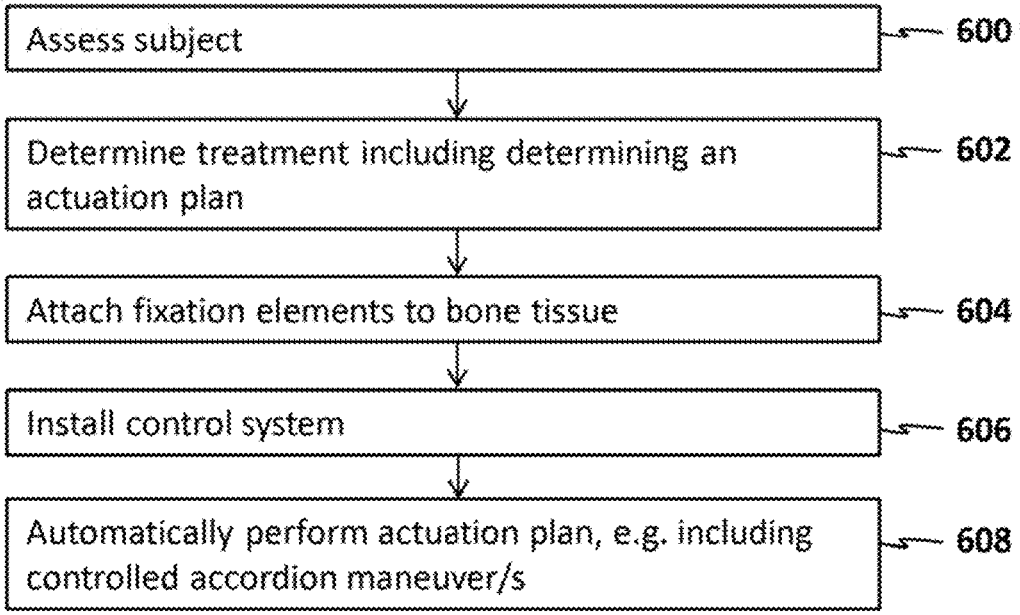
FIG. 6B is a method of bone treatment, according to some embodiments of the disclosure.

FIG. 6B is a method of bone treatment, according to some embodiments of the disclosure.

At 600, a subject may be assessed. Where a physician and/or other healthcare professional (HTC) may provide a diagnosis based on one or more type of assessment. For example, based on one or more of direct physical assessment/s of the patient, imaging data, blood test data, physiological data (e.g., blood pressure, weight), patient grouping data (e.g., age, sex). The diagnosis may include providing a diagnosis of one or more bone condition.

At 602, a treatment type may be determined, for example, in response to the diagnosis and/or assessment data. For example, where a healthcare professional (HCP)(e.g., physician) may recommend a treatment, based on the diagnosis e.g., a bone repositioning treatment.

The treatment may include a surgery (e.g., to cut bone and/or install bone fixation element/s and/or a device) and may include desired movements to bone portions e.g., after the surgery. Where, the desired movements may be in the form of an actuation plan including instructions to perform bone positioning movement/s and/or accordion maneuver/s.

Feature/s of the actuation plan may be decided by the HCP, for example by the HCP selecting option/s and/or inputting data to a control system e.g., through one or more user interface connectable to the control system.

Where the HCP may input and/or select one or more of frequency, amplitude, duration of accordion maneuver/s to be performed, for example, in context of bone positioning movements to the bone tissue (which the HCP may also input and/or select).

In some embodiments, feature/s of the actuation plan may be generated automatically, for example, using subject data. For example, where imaging and/or HCP inputted subject data may be used to generate feature/s of bone movement and/or accordion movement plans.

In some embodiments, the subject data includes a model including spatial relationships between bone tissue and the adjustable fixation device e.g., the model using initial and/or desired spatial relationships. Where the model may be received or generated using imaging and/or inputted data (e.g., inputted by one or more HCP).

In some embodiments, the model includes spatial relationships between portion/s of the adjustable fixation device including, for example, how length change in individual struts changes spatial relationship between the first and second fixation elements, and, in some embodiments, thus bone tissue.

Where, in some embodiments, the actuation plan is generated based on selected features (e.g., one or more of frequency, amplitude, duration of accordion maneuver/s to be performed, for example, in context of bone positioning movements to the bone tissue) and spatial relationships of the model.

At 604, one or more bone fixation element (e.g., fixation element/s 110, 112 FIG. 1, fixation element/s 310, 312 FIG. 3, fixation element/s 410, 412 FIG. 4, fixation element/s 510, 512a-c FIG. 5A, fixation element/s 803, 805 FIGS. 8A-B, fixation element/s 903, 905 FIGS. 9A-B) may be attached to bone tissue of the subject. For example, during a surgical procedure where bone tissue is optionally cut and/or repositioned.

At 606, a control system is installed, for example, as part of installation of a bone fixation device, e.g., during and/or after the surgical procedure. Where the bone fixation device may be installed (e.g., attached to bone fixation element/s) and then the control system is connected to the bone fixation device. Or where the bone fixation device with the control system already connected, is attached to the bone fixation element/s.

At 608, the control system automatically performs controlled accordion maneuver/s, e.g., according to the actuation plan of step 602. The controller (e.g., upon waking at a specified time) may instruct actuator/s of the control system to perform the specified accordion maneuver/s e.g., at specified time/s. Where, (e.g., as described regarding FIG. 5A) the actuator/s may be associated with struts and may be configured to change a dimension of the strut/s (e.g., struts 507 and actuators 511 FIG. 5A) to perform the accordion maneuver/s. As described elsewhere in this document, the actuation plan may be subject to change e.g., based on feedback.

Figure 7:
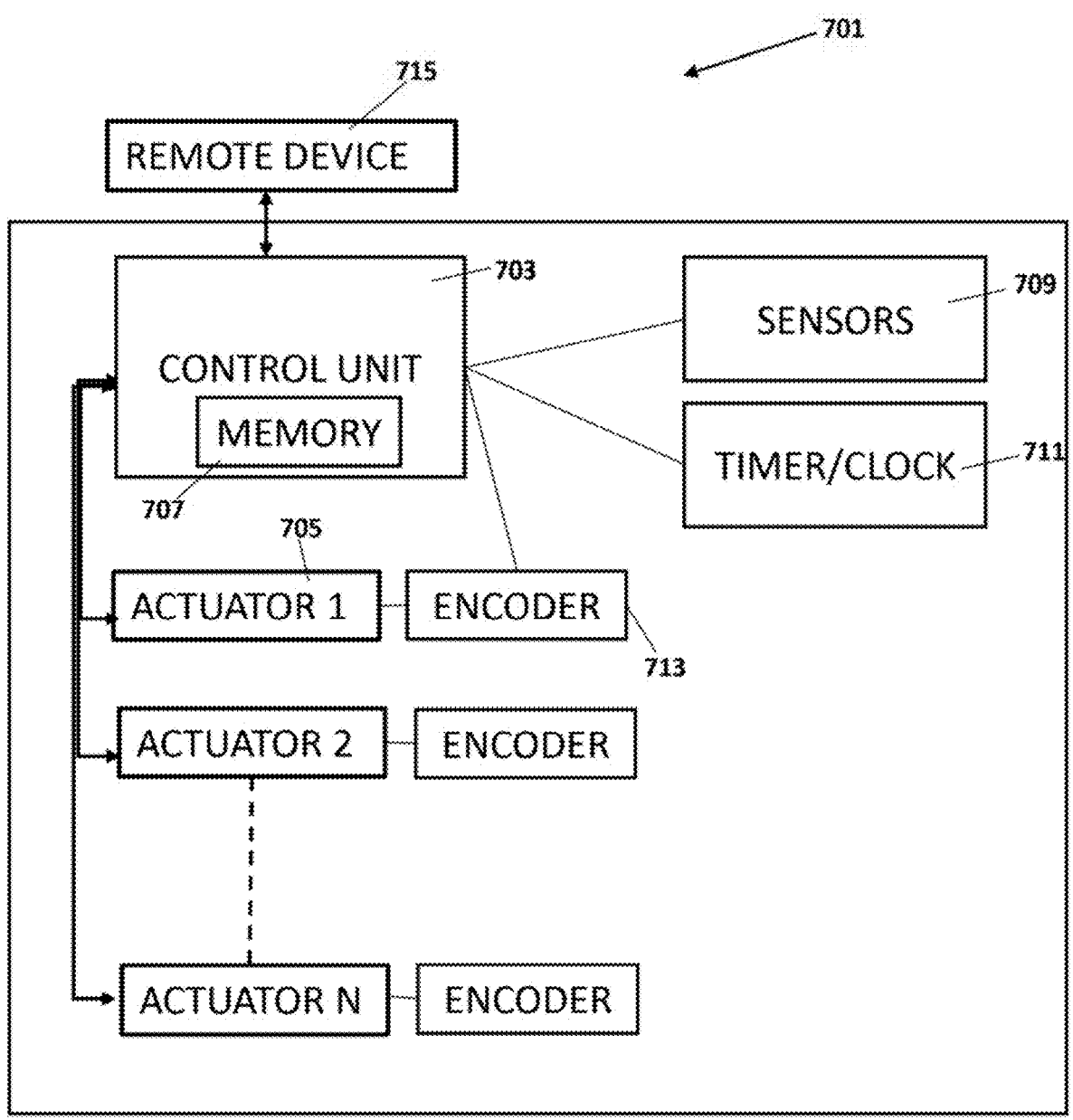
FIG. 7 is a block diagram of a control system for use with an adjustable bone fixation device, according to embodiments of the presently disclosed subject matter.

FIG. 7 is a block diagram of a control system for use with an adjustable bone fixation device, according to embodiments of the presently disclosed subject matter.

As described hereinabove, in some embodiments, control system 701 includes a control unit 703 for controlling the plurality of actuators 705. In some embodiments, the control unit operates the actuators according to an actuation plan stored at a memory 707 of the control unit.

In some embodiments, control unit 703 is configured to obtain readings from one or more sensors 709 of the system.

In some embodiments, the sensors 709 include one or more sensors 710 that are configured for measuring system-related parameters, such as actuator-related parameters, for example, measure the torque generated by the actuator which is indicative of the axial force applied onto the strut. In some cases, one or more sensors are configured for measuring the torque and/or a parameter indicative of the torque, for example, for measuring the current consumption of the actuator (e.g., a current meter or sensor). Since, in some embodiments the actuator is configured to directly drive the adjustment of the strut, a correlation exists between consumption of electrical current by the actuator and the torque generated the actuator (e.g., when brushed motors are used), and/or between the rotation speed of the actuator and voltage, and the torque generated by the actuator (e.g., when brushless motors are used). In some embodiments, sensors 709 include one or more sensors 712 that are configured for measuring conditions related to the surroundings of the device, and/or to external factors which may have an effect on device operation. Examples of such sensors include: a temperature sensor and/or a humidity sensor, since, for example, extreme temperature conditions may affect operation of the actuator and/or of the circuitry;

a sensor configured for detecting the current posture of the patient, since, for example, in a patient standing up the load acting on the device would be higher as compared to when the patient sits or lies down;

a sensor configured for detecting a current orientation of the body part to which the device is connected, since, for example strut adjustment and/or actuator operation may be affected by the orientation and/or the load acting on the device in a certain orientation;

an acceleration sensor or an impact sensor, since, for example, it would be preferred to adjust the strut whilst the patient is still and not moving;

a weight/load sensor.

The sensors may be positioned with respect to the bone fixation device based on their function, for example, a weight/load sensor can be positioned between a strut and the frame portion to which it is connected and/or within the strut itself, so as to identify the load acting on it; a temperature/humidity sensor can be positioned externally on the frame portions, and/or positioned with respect to the control system (e.g., embedded within or mounted on a housing of the control unit, embedded within or mounted on a housing of an actuator); etc.

Referring back to the block diagram, in some embodiments, the system includes a timer and/or a clock 711, which can be utilized by the control unit for timing operation of the actuators according to the actuation plan; for monitoring a duration of actuation and/or monitoring the time it takes to complete a planned adjustment of a strut; monitoring a time interval between successive actuations; and/or other time or timing related factors.

In some embodiments, each of the actuators is coupled to an encoder 713, which is in communication with the control unit. The encoder tracks the speed and/or position of the moving part (e.g., shaft, rotor) of the actuator. Based on the feedback received from the encoder, control unit 703 can determine the change in the length of the strut, and/or a relative position of the strut, and/or a speed in which the strut is adjusted.

In some embodiments, based on input received from the sensors, the clock/timer, and/or the encoder(s), the control unit is configured to determine the extent of adjustment and to identify whether the adjustment had been carried out according to the actuation plan.

In some embodiments, one or more components of the control system 701, for example the control unit 703, are in communication with a remote or external device 715. The remote device may include a cellular phone, a wearable device, a remote computer, a tablet, a remote server, an information storage cloud. In some cases, the control system communicates with a remote device of the patient or a caregiver, a physician, or other.

Exemplary Treatments

Figures 8A, 8B:
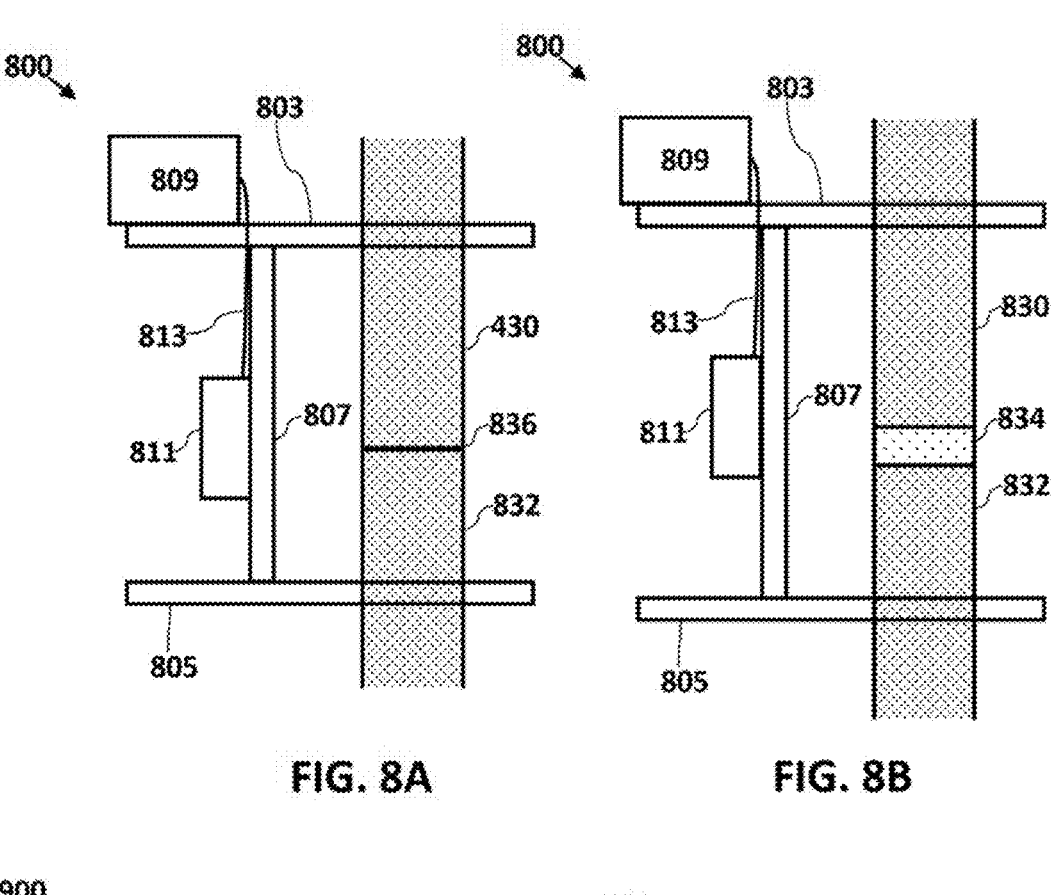
FIGS. 8A-B are simplified schematic of an adjustable bone fixation device connected to a bone, according to some embodiments of the disclosure.

FIGS. 8A-B are simplified schematic of an adjustable bone fixation device 800 connected to a bone 830, 832, according to some embodiments of the disclosure.

FIGS. 8A-B may illustrate a same device 800 at different times during treatment of bone 830, 832. Where forces applied to two parts of a bone, 830, 832 by expansion of a strut 807 may act to produce growth of new bone tissue 834 at a fracture site 836. Where strut 807 may be attached between a first fixation element 803 attached to a first bone portion 830 and a second fixation element attached to a second bone portion 832. A controller at least partially housed in a controller housing 809 may send control signals (e.g., via a data cable 813) for control of activations of an actuator 811. Where actuator 811 may be configured to change a length of strut 807 e.g., from an initial length illustrated in FIG. 8A to an end length illustrated in FIG. 8B.

FIGS. 8A-B illustrate an embodiment where the repositioning of bone portions 830, 832 includes tensile forces e.g., applied to overcome resistance to movement associated with new bone tissue 832 generation. Where, for example, as described in more detail hereinbelow, accordion maneuver/s may be applied by strut 807 to fixation elements 803, 805 and thereby to bone tissue. Where forces applied to bone tissue via the accordion maneuver/s may include compression. For example, compression and tension reciprocally e.g., associated with change in strut 807 length.

Figures 9A, 9B:
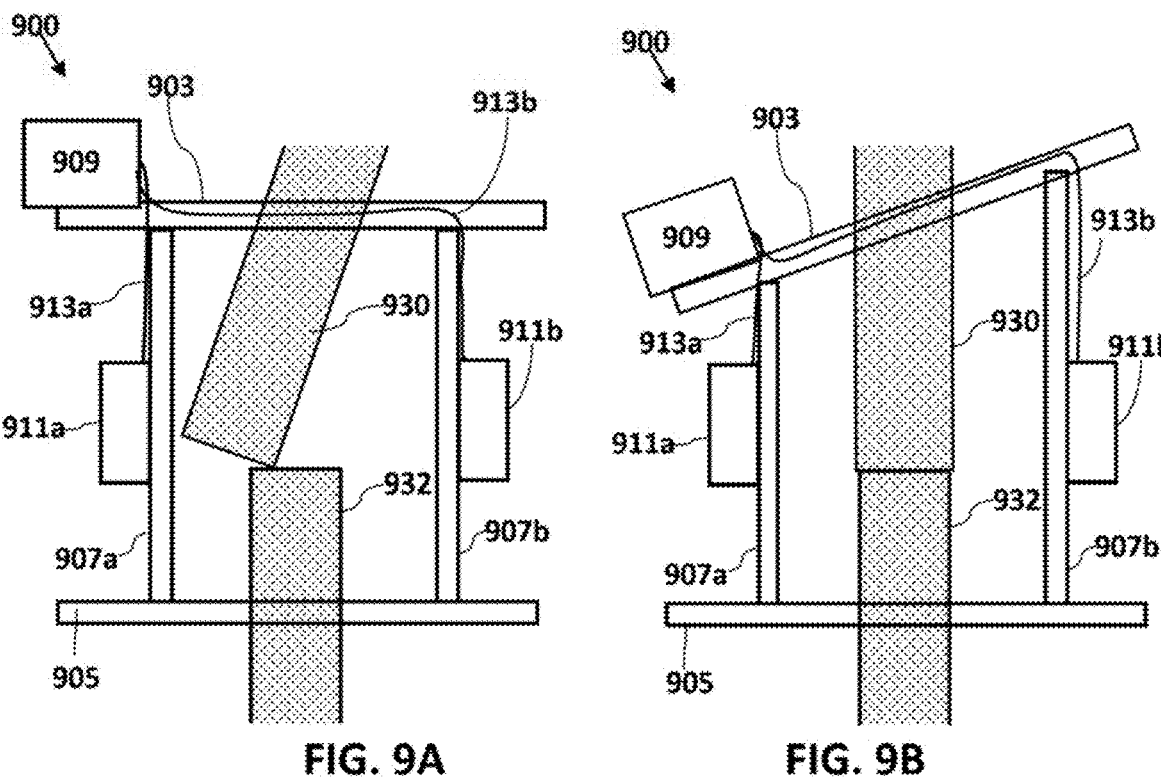
FIGS. 9A-B are simplified schematic of an adjustable bone fixation device connected to a bone, according to some embodiments of the disclosure.

FIGS. 9A-B are simplified schematic of an adjustable bone fixation device 900 connected to a bone 930, 932, according to some embodiments of the disclosure.

FIGS. 9A-B may illustrate a same device 900 at different times during treatment of bone 930, 932. Where forces applied to bone, 930, 932 by expansion of a strut 907*b* and contraction of a strut 907*a* may act to reposition bone portions 930, 932.

Where struts 907*a-b* may be attached between a first fixation element 903 attached to a first bone portion 930 and a second fixation element attached to a second bone portion 932. A controller at least partially housed in a controller housing 909 may send control signals (e.g., via a data cables 913*a-b*) for control of activations of actuators 911*a-b*. Where actuators 911*a-b* may be configured to change lengths of strut 907*a-b* respectively e.g., from initial lengths illustrated in FIG. 9A to end lengths illustrated in FIG. 9B.

FIGS. 9 A-B illustrate an embodiment where the repositioning of bone portions 830, 832 includes application of torque e.g., to bone portion 930. Where, for example, as described in more detail hereinbelow, accordion maneuver/s may be applied by strut/s 907*a-b* to fixation elements 909, 905 and thereby to bone tissue.

Dynamization forces, for example, applied during accordion maneuver/s, by a device including multiple struts may include one or more of tensile, compressive, and torque. For example, application of torque force and/or rotational movement/s as effected by shortening of a strut 907*a* and lengthening of an opposing strut 907*b* may be applied during bone positioning and/or during accordion maneuver/s. Including where the positioning involves only axial movement e.g., as provided by tensile (or compressive) forces e.g., as illustrated in FIGS. 8 A-B.

Exemplary Timing and/or Exemplary Actuation Plans

Figure 10A:
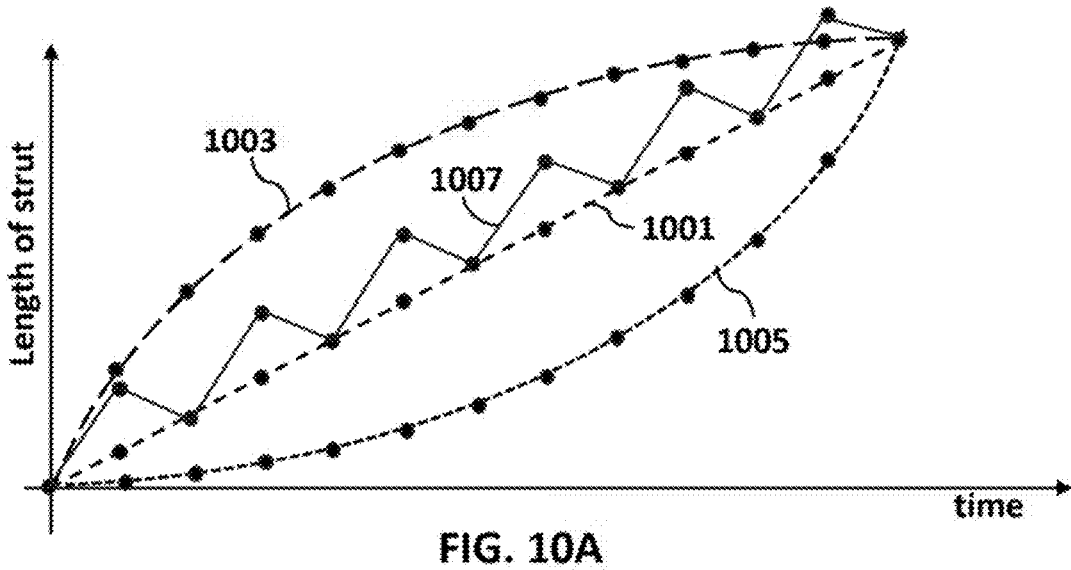
FIG. 10A is a simplified schematic plot of strut length with time, according to some embodiments of the disclosure.

FIG. 10A is a simplified schematic plot of strut length with time, according to some embodiments of the disclosure.

In some embodiments, FIG. 10A illustrates different exemplary embodiments of actuation plans.

Plot 1001 illustrates an exemplary bone positioning actuation plan where strut length changes are uniform. Where the solid dots may illustrate strut length with time, and line 1001 may illustrate a trend, e.g., as opposed to showing the speed of the individual strut length changes which, for example, may be too rapid with respect to time between actuations to change length of the strut. For example, in some embodiments, each dot illustrates one or more actuation changing the strut length from the previous dimension illustrated by a dot, the time required being e.g., in a scale of minutes, where time between strut length changes may be at a different scale e.g., hours.

Plots 1003 and 1005 illustrate exemplary bone positioning actuation plans where size of the repeated strut length changes over time.

Plot 1003, for example, illustrating an actuation plan where length changes reduce in magnitude with time. A potential benefit being reduced discomfort to a patient where, at a beginning to treatment where tissue (e.g., bone and/or soft tissue at the treatment site) may be less dense and/or healed, larger movements to bone portions as effected by changing strut length may be performed, but, later in the treatment, where healing has progressed and/or tissue density has increased strut length changes may be smaller in magnitude.

Plot 1005, for example, illustrating an actuation plan where length changes increase in magnitude with time. A potential benefit being reduced discomfort to a patient, where, at the beginning of treatment, when, for example, the patient has recently undergone surgery, magnitude of strut length changes may be smaller, but, where healing has progressing, later in the treatment, strut length changes may be larger in magnitude.

Although FIG. 10A illustrates exemplary scenarios where a frequency of strut length changes as illustrated by the solid points is uniform, in some embodiments, strut length changes may be performed more or less frequently.

Figure 10B:
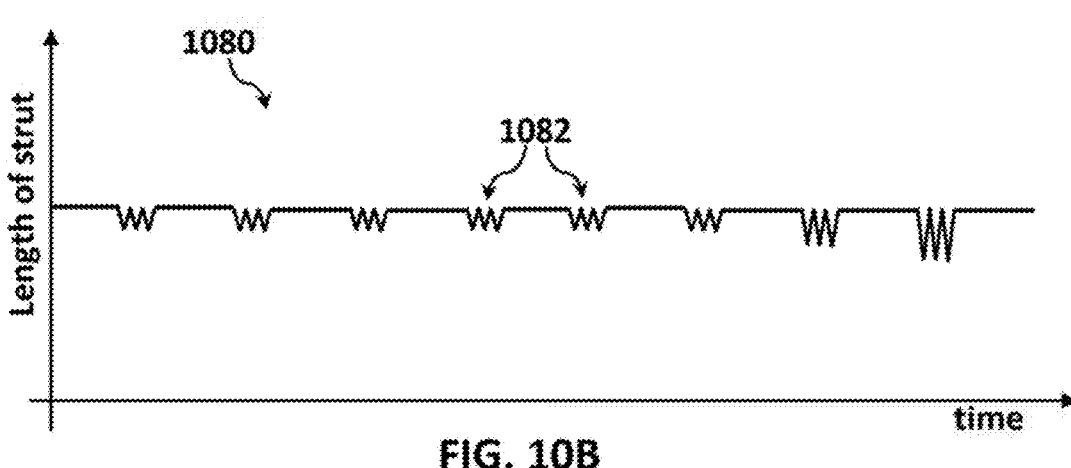
FIG. 10B is a simplified schematic plot of strut length with time, according to some embodiments of the disclosure.

FIG. 10B is a simplified schematic plot of strut length with time, according to some embodiments of the disclosure.

In some embodiments, FIG. 10B illustrates exemplary accordion maneuvers with time. For example, illustrates an accordion maneuver actuation plan which e.g., may be overlaid with a bone actuation plan to provide an overall treatment actuation plan. For example, returning to FIG. 10B, plot 1007, in some embodiments, illustrates bone movement actuation plan 1001 combined with an accordion actuation plan where, for each bone positioning actuation, an accordion actuation is performed, a time period of two bone positioning actuations (as represented by data point dots of plot 1007) providing a reciprocal overall movement.

Where plot 1080 illustrates a plurality of groups 1082 of accordion maneuvers. As illustrated, in some embodiments, magnitude of accordion maneuvers may change over time. Alternatively or additionally, frequency of performance of accordion movements may change over time and/or number of actuations/movements per set.

For example, one or more of magnitude or frequency of performance of sets of accordion movements, or number of movements in each set increasing with time.

For example, one or more of magnitude or frequency of performance of sets of accordion movements, or number of movements in each set decreasing with time.

For example, where one or more of magnitude or frequency of performance of sets of accordion movements, or number of movements in each set are selected based on a stage of treatment e.g., small prior to a start to bone movement actuations, larger during a time of bone positioning and/or during a consolidation time period.

For example, where one or more of magnitude or frequency of performance of sets of accordion movements, or number of movements in each set are selected and/or adjusted based on feedback measurements.

In some embodiments, size of bone positioning movements and/or amplitude of accordion maneuver movements may vary during treatment. For example, on a daily basis. For example, during a timescale of the treatment (e.g., the size and/or amplitude associated with a stage of the treatment).

In some embodiments, accordion maneuvers are only performed during portions of a total treatment. For example, only during consolidation. For example, according to a treatment plan specified by and/or selected by and/or generated based on input of a clinician.

In embodiments where the size of bone positioning movements and/or amplitude of accordion maneuver movements vary during a day, bone movement/s may be concentrated at night time e.g., for patient comfort. Where, for example, optionally equally temporally spaced bone positioning and/or accordion maneuver actuation sets may increase in magnitude over a duration of 24 hours.

For example, an exemplary plan including 20 bone movement sessions (bone positioning and/or accordion maneuver actuation/s performed in each session) in a time period (e.g., a day) may start with 5 movements having magnitude ×, then 10 movements having magnitude 2× and then the final 5 movements with magnitude of 3×.

FIGS. 10C-16 are simplified schematics plot of strut length with time, according to some embodiments of the disclosure.

Although FIGS. 10C-16 illustrate accordion maneuver/s as including changes in strut length, which corresponds to some described embodiments herein, the FIGS. 10C-16 should be understood to also illustrate relative timing of application of dynamization force/s and/or dynamization actuator actuation/s (which may not include change in strut length) with respect to bone positioning actuations.

Although each of FIGS. 10C-16 illustrate overall (e.g., "net") positive (extension) changes in strut length, it should be understood that concepts and methods as described regarding FIGS. 10C-16 may be employed for strut/s which have overall (e.g., "net") negative (contraction) change in strut length.

Figure 10C:
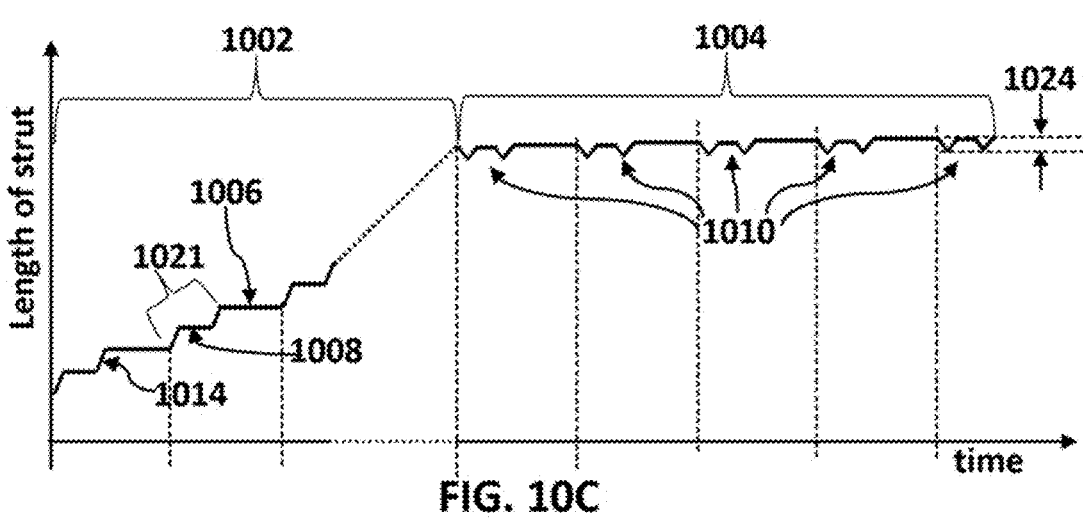

FIG. 10C illustrates an exemplary treatment actuation plan where an active phase 1002, also herein termed a "bone positioning" phase is followed by an accordion maneuver phase 1004.

Bone positioning phase 1002 may include repeated changes in strut length 1014, each change followed by a rest period of time 1006 where the strut length remains constant. Where, in some embodiments, rest periods 1006 may have duration of 1 minute to 24 hours.

Where, in an exemplary embodiment, a plurality of changes in strut length occurs each day e.g., dashed vertical lines in FIG. 10 representing weeks. A total duration of the bone positioning phase may be 1 week-6 months, or 1-3 months, or lower or higher or intermediate durations or ranges. Where the duration may depend on one or more of amplitude of individual positioning movements, a number of positioning movements, and a total desired movement for the bone portion/s.

Rest periods 1006, 1008 may have different durations, for example, groups 1021 of strut length changes may occur where individual strut length changes of the group are separated from each other by short rest periods 1008. Where groups 1021 (e.g., each group) may be followed by an extended rest period 1006. Where groups 1021 of strut length changes may be performed during a subject's waking hours and extended rest periods 1006 may, for example, occur during the subject's sleeping hours.

Accordion maneuver phase 1004 may include one or more group 1010 of accordion maneuver movements (corresponding to accordion maneuver actuations) including back and forth strut length changes. Where the back and forth strut changes may be controlled to maintain an initial strut length after the group of movements 1010 have been performed.

Groups of accordion maneuver movements may include 2-50 movements, or 2-20 movements, or lower, or higher, or intermediate numbers of movements.

Each strut dimension change of the group may have an amplitude 1024 of 0.01-1 mm, or 0.01-5 mm, 0.05-1 mm, or 0.1-0.5 mm, or lower, or higher, or intermediate amplitudes or ranges. The back and forth movements may each have the same amplitude or the amplitude may vary from movement to movement and/or between groups 1010.

Where each movement (e.g., a strut expansion or a strut contraction) may have a duration of 0.1-5 seconds, or 0.5-2 seconds, or lower, or higher, or intermediate, durations, or ranges.

Groups of movements may include oscillating strut dimensions, where a frequency of the oscillations may be 0.01-20 Hz, or 0.01-10 Hz, or 0.5-5 Hz, or 0.01-1 Hz, or 0.1-1 Hz, or 0.5-1 Hz, or lower than 1 Hz, or lower or higher or intermediate frequencies or ranges.

Groups of accordion maneuver actuations 1010 may occur a plurality of times, for example, more than once a day. For example, at a frequency of between 30 minutes and 24 hours. Where rest time periods may occur between the actuations and/or the groups of actuations.

One or more of the above quantifications for amplitude, duration, oscillation frequency, and frequency of performing accordion maneuver actuation groups may be applicable to the scenarios of one or more of FIG. 10B and FIGS. 11-16.

Alternatively or additionally to accordion maneuver/s phase 1004 including illustrated strut length changes, accordion maneuver/s phase 1004 may include one or more other type of dynamization actuations e.g., as described elsewhere in this document.

Figure 11:
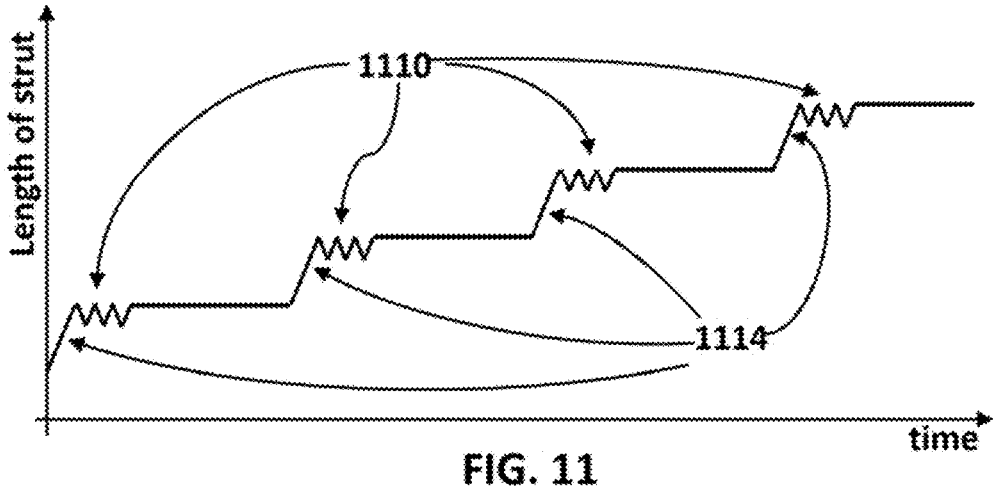

Referring now to FIG. 11, in some embodiments, accordion maneuver/s actuation/s 1110 (e.g., corresponding to strut length changes may accompany (e.g., occur during a same time period) as bone positioning actuations 1114.

Where accordion maneuvers may not effect a total duration of the treatment, where the accordion maneuvers are timed to occur between bone positioning movements which occur according to a schedule e.g., which is independent of the accordion maneuvers and/or according to a treatment plan used in treatment without accordion maneuvers.

Alternatively, accordion maneuvers may increase a total duration of the bone repositioning treatment e.g., where the accordion maneuvers are performed during a "pause" in bone positioning treatment e.g., where the accordion maneuvers delay bone positioning movements and/or are associated with a lower rate of bone repositioning. Where, although FIG. 11 illustrates accordion maneuver/s actuations 1110 as including alternating direction strut actuations, accordion maneuver/s actuations 1110 may alternatively or additionally include other type/s of dynamization actuation, e.g., as described elsewhere in this document.

Where dynamization actuations 1110 may be, e.g., as illustrated in FIG. 11, immediately or shortly following (e.g., within 30 mins of) positioning actuations 1114. Alternatively or additionally, dynamization actuations 1110 may precede immediately or shortly before (e.g., up to 30 mins prior to) positioning actuations 1114. Although, in FIG. 11, each positioning actuation 1114 is closely temporally associated with a group of dynamization actuations 1110, fewer than all of the positioning actuations may be associated with a respective group of dynamization actuations.

Figure 12:
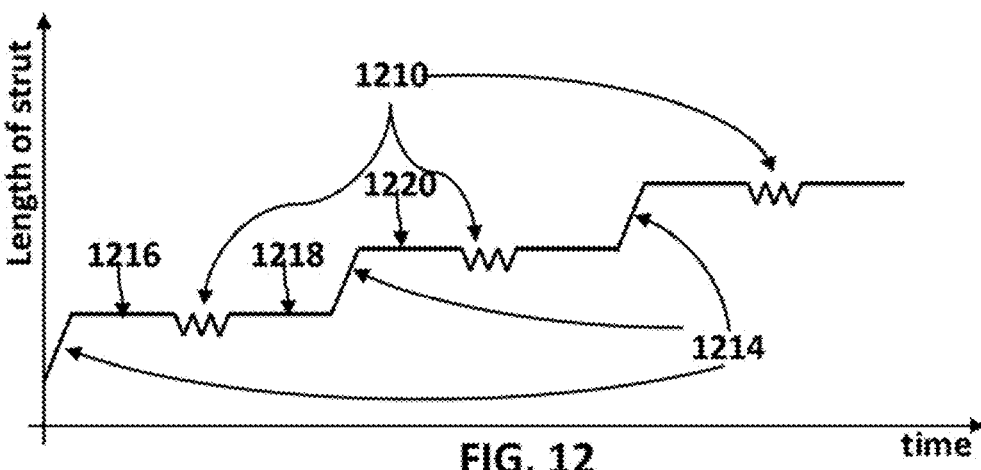

Referring now to FIG. 12, dynamization actuation groups 1210 may occur at separate times. For example, rest periods occurring prior 1216 and after 1218 dynamization actuations 1210 and/or prior 1218 and after 1220 a positioning actuation 1214 (or group of positioning actuations).

Dynamization actuations 1210 may alternate with positioning actuations 1214 e.g., as illustrated in FIG. 12. For example where a time duration illustrated in FIG. 12 is a day; a plurality of times a day positioning actuations 1214 may occur alternating with a plurality of dynamization actuation groups 1210.

Alternatively, a plurality of bone dynamization actuation groups may be performed (with rest periods therebetween) and/or a plurality of bone positioning actuations (with rest periods therebetween) where, during a time period (e.g., a day) both bone dynamization actuations and bone positioning actuations are actuated.

Figure 13:
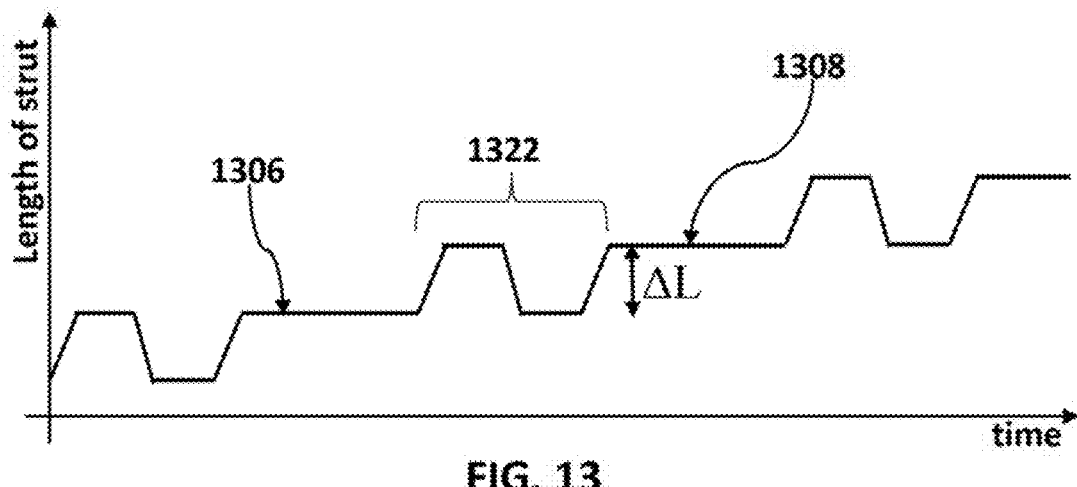

Referring now to FIGS. 13-14, groups of actuations may include a combined effect of positioning and bone dynamization. For example, where a plurality of actuations (a group of actuations) including one or more extension and one or more contraction result in a net change in length ΔL.

Referring to FIG. 13, extensions and contractions may be equal in length, an un-even number of extensions (in FIG. 13 two extensions and one contraction for each actuation group 1322) provides the net change in length ΔL. Where each activation group may be preceded 1306 and/or followed by a rest period 1308.

Referring to FIG. 14, extensions and contractions may have different lengths, for example, to provide a net change in length ΔL. Where a plurality of actuations 1422 including one or more contraction and one or more extension may include contractions associated with a larger cumulative strut length change than extensions to provide the net change in length (or vise-versa regarding extensions and contractions).

For example, in some embodiments, bone lengthening actuation plans may have a total desired extension or movement for a period of time e.g., a daily desired extension is performed by a plurality of extensions and contractions.

For example, an actuation plan may include back and forth movements where an extension (or a cumulative extension) over a time period has a larger dimension than a contraction (or a cumulative contraction) over a time period.

Where extensions and contractions are, for example, of one or more struts and/or of a space between the fixation elements and/or of a longitudinal length of the bone tissue.

In an exemplary embodiment, a total of 1 mm extension in a time period (e.g., per day) is achieved by 20 separate movements, where some of the separate movements are extensions and some contractions. In some embodiments, the extensions and/or contractions have equal magnitude. For example, where a proportion (e.g., half, e.g. 10) of the movements are extensions of 0.3 mm and a proportion (e.g., half, e.g. 10) of the movements are contractions of 0.2 mm. In this case, in a time period (e.g., a day) a total extension is of 3 mm and a total contraction is 2 mm giving a net extension of 3 mm. In another exemplary embodiment, a total extension is 2 mm and a total contraction is 1 mm giving a net extension of 3 mm.

For lengthening actuation plans (e.g., the movements together providing bone positioning and accordion maneuver movements to tissue) total extensions for a time period (e.g., daily until a target position is reached) may be of 1-5 mm, with total contractions of 0.1-4.5 mm.

Referring now to FIG. 15 and FIG. 16 which may illustrate bone positioning strut length changes 1514 and dynamization strut length changes 1610. FIG. 15 and FIG. 16 may have a same scale.

Where bone positioning strut length changes 1514 may have larger magnitude ΔL than a magnitude δL of accordion maneuver strut length changes 1610. Where bone positioning strut length changes 1514 may have a slower rate of change than accordion maneuver strut length changes 1610.

In some embodiments, more than two actuations, optionally spread out over time, may be used to provide an accordion maneuver. For example, where a plurality of strut extensions (e.g., to provide tensile force to the bone treatment site) may be followed or preceded by one or more strut contractions (e.g., to provide compressive force). For example, where one or more strut extensions may be followed or be preceded by a plurality of strut contractions. Where the extension/s may have different temporal and/or amplitude feature/s than the contraction/s.

In some embodiments, the extensions may have a same amplitude as contractions (e.g., in total or where each extension corresponds to a like sized contraction).

Where an exemplary accordion movement actuation plan may include a distraction (e.g., by 4 mm) over a first time period (e.g., 8 days) followed by compression having the same magnitude as the distraction (e.g., by 4 mm) completed over a second time period which may have the same duration as the first time period (e.g., 8 days).

The first time period may be different to the second time period. For example, where "docking union" may be implemented by providing a distraction over a first time period and a contraction (optionally of the same magnitude as the distraction) over a second time period which is shorter or longer than the first time period: For example, where a distraction of 2 mm is provided over 4 days, and compression of 2 mm is provided over 2 days.

In some embodiments, an accordion actuation plan is repeated until union of bone and/or docking union is identified and/or diagnosed. Where bone union may include where healing of the bone fracture e.g., with continuous sufficiently dense bone tissue. Where docking union may include where a bone fragment reaches a final position with respect to another bone fragment e.g., where portion/s are sufficiently close to each other and/or are in contact and/or have interlocking and/or interleaving portions.

In some embodiments, accordion maneuvers where there is no net change in position of bone portions may be employed during one or more of a latency period, a consolidation period, and during treatment of bone non-union where a fracture does not properly unite.

Exemplary Use of Exemplary Feedback

FIG. 17 is a method of bone treatment and/or diagnosis, according to some embodiments of the disclosure.

At 1700, in some embodiments, fixation elements of an adjustable bone fixation device are moved with respect to each other e.g., via change in length of one or more strut connecting the fixation elements. For example, as illustrated and/or described regarding FIG. 5A and/or FIG. 5B and/or FIGS. 8A-B and/or FIGS. 9A-B.

At 1702, in some embodiments, measurement/s indicative of force required to produce the movement are received. The measurement/s supplied by one or more sensor/s, for example, sensors 709 and/or sensors 712 as described regarding FIG. 7. Where, for example, the measurement/s received include measurements indicative of torque generated by one or more actuator. Where the torque is indicative of axial force applied onto the strut/s. In some cases, measurement/s received include measurements from one or more sensors configured for measuring the torque and/or a parameter indicative of the torque, for example, sensor/s for measuring the current consumption of the actuator (e.g., a current meter or sensor). In some embodiments, current consumption for a plurality of actuators concurrently moving the fixation elements (e.g., each actuator moving a strut, a plurality of struts connecting the fixation elements) is received.

In some embodiments, axial force measurements may be adjusted using measurements of actual change in strut length. For example, in some embodiments, current consumption measurements may be adjusted and/or compensated using encoder measurements (e.g., from one or more encoders 713 FIG. 7). Where, in some embodiments, encoder measurements may be indicative of actual movement and/or change in length of struts.

At 1704, in some embodiments, one or more tissue feature is determined, using the one or more measurements and feature/s of the movement/s performed at 1700. Where, in some embodiments, one or more measurement of force applied is used to determine density and/or strength of tissue under one or both of tensile and compressive force. In some embodiments, an average of a plurality of measurements is used. For example, where a plurality of struts are actuated to effect a movement between the fixation elements, an average current consumption of the plurality of struts may be used. For example, referring back to FIG. 5A, an average current consumption for all of or a subset of actuators 511 may be used. In some embodiments, additionally or alternatively to using the average current consumption, a standard deviation between current consumption measurements is used to determine tissue feature/s.

FIG. 18 is a method of performing an actuation plan, according to some embodiments of the disclosure.

At 1800, an actuation plan including bone positioning actuations and optional accordion maneuver actuations may be received. The actuation plan may be generated according to user (e.g., physician) specifications. The actuation plan may be adjusted or generated according to received inputs. The inputs including, for example, patient data e.g., age, treatment type, dimensions of the treatment site, measurement data (for example, imaging data e.g., x-ray). The inputs including, for example, user (e.g., physician) specifications and/or goals. The inputs including, for example, patient specifications and/or goals. Where the inputs may be received by a controller which then may generate and/or adjust the actuation plan. Alternatively, a remote device (e.g., 715 FIG. 7) may generate and/or adjust the actuation plan and provide it to the controller.

At 1802, a portion of the activation plan may be performed, optionally while acquiring measurement/s. Measurements may include one or more of current consumption measurement for one or more actuator, and/or sensor data e.g., encoder data, torque sensor data.

At 1804, optionally the subject is assessed, for example, by a physician and/or using imaging of the treatment area. Where, a quality of bone growth associated with the bone positioning and/or accuracy of the bone positioning may be assessed.

In some embodiments, measurement data may be used in assessment of the subject. Force feedback (e.g., as determined from one or more sensor measurement), for example, may be used as an indication of bone growth and/or level of consolidation of the bone growth. For example, if tensile forces required to change a length (e.g., extend) of one or more strut are identified as being low (e.g., as relative to expected force e.g., for the individual subject), a clinical situation of non-union may be identified.

At 1806, the actuation plan may be verified or adjusted, based on the assessment at step 1804 and/or based on measurements received at step 1802.

For example, where insufficient bone growth and/or callus formation is identified, accordion maneuver actuations may be added to the actuation plan e.g., delaying positioning actuations of the actuation plan or accompanying positioning actuations of the actuation plan. Where addition includes incorporating accordion maneuver actuation/s when previously absent in the actuation plan or an increase in intensity and/or amount and/or duration of accordion maneuver actuations.

For example, where non-union of bone portions is identified, the actuation plan may be adjusted to return the bone positions towards each other e.g., to enable union of the bone portions.

FIG. 19 is a method of performing an actuation plan, according to some embodiments of the disclosure.

At 1900, an actuation plan including accordion maneuver actuations is received, for example, including one or more feature of step 1800 FIG. 18.

At 1902, accordion maneuver actuations according to actuation plan may be initiated. Where the accordion maneuver actuations may be configured to change a strut dimension (e.g., length), for example, of strut/s 507 FIG. 5A.

At 1904, measurement feedback regarding the actuation, optionally during actuation is received. For example, according to one or more feature of step 1702, FIG. 17. At 1906, the measurement feedback is evaluated.

Evaluation may include comparison of measurement/s with a threshold value. Where, in an exemplary embodiment, the actuation is performed until a threshold measurement is reached. Potentially providing verification that the accordion maneuver actuation applies sufficient force to the tissue.

At 1908, upon verification of the actuation at step 1906, the actuation is continued according to actuation plan (where steps 1904 and 1906 may be performed one or more additional times) or the actuation is finished.

At 1910, optionally, the current actuation is adjusted based on received measurements. For example, an actuation may be terminated upon a received measurement reaching a threshold. Where the measurement may be an indicator of position and/or load.

At 1912, optionally, the actuation plan is adjusted based on received measurements.

Exemplary Detailed Method

FIGS. 20A-B are a flowchart of a method of bone treatment, according to some embodiments of the disclosure.

Referring to FIG. 20A, at 2000, in some embodiments, an adjustable bone fixation device (e.g., device 501 FIG. 5A) is attached to patient bone tissue, for example, during a surgical procedure. For example, according to one or more feature of step 604 FIG. 6. Where, for example, a first fixation element (e.g., fixation element 503 FIG. 5A) of the device is attached by at least one connector (e.g., transfixion pin 510 FIG. 5A) to bone tissue, and a second fixation element (e.g., fixation element 505 FIG. 5A) of the device is attached by at least one connector (e.g., transfixion pins 512*a*-*c* FIG. 5A) to bone tissue e.g., the first and second fixation elements attached at either side of a treatment site e.g., bone fracture and/or cut.

At 2002, in some embodiments, optionally, a model is received of the treatment site. The model including, for example, relative spatial location of bone tissue portions and of portion/s of the adjustable bone fixation device. In some embodiments, the model includes an initial configuration of the tissue and fixation device e.g., immediately or shortly after (e.g., within a day or week) of performing step 2000. Optionally, the model includes projected future spatial locations between bone tissue and the adjustable fixation device as a bone positioning actuation plan is implemented.

In some embodiments, an actuation plan is received. Where the actuation plan may include a bone position actuation plan and/or an accordion maneuver actuation plan. In some embodiments, the actuation plan is generated using the model. Where, for example, details (length and/or speed and/or duration of one or more actuation) of movements of individual struts for accordion maneuvers of the accordion maneuver actuation plan may be generated based on the spatial relationship/s of the model. For example, where, in some embodiments, during bone positioning, a subset of struts most aligned with an axis of bone tissue are used to provide accordion maneuvers.

In some embodiments details of tissue testing are received e.g., the testing as described regarding step 2006 and/or 2018. For example, thresholds for force required to move bone tissue.

At 2004, in some embodiments, tissue testing measurement/s are acquired and/or received. Where, in some embodiments, acquisition of measurement/s includes moving fixation elements of the adjustable fixation device (e.g., according to feature/s of step 1700 FIG. 17). In some embodiments, the movement/s are performed according to the actuation plan received at step 2002. In some embodiments, movements of the actuation plan are adjusted based on the model. For example, where a tissue testing actuation plan includes magnitude and/or timing of actuations to be performed, which actuators perform the tissue testing actuations may be determined using the model.

At 2005, in some embodiments, one or more tissue features are determined. Where, for example, an extent of healing of the tissue post-operatively is determined. In some embodiments, the tissue features are determined using the measurements acquired at step 2004. For example, by comparing force measurement/s (e.g., current consumption measurement/s) with a threshold e.g., a threshold received at step 2002.

At 2006, in some embodiments, the one or more tissue features determined at 2005 are evaluated. Where, in some embodiments, the tissue features are evaluated to verify (or not) that the tissue is suitable (e.g., sufficiently healed) for osteogenesis to be performed.

In some embodiments, step/s 2004, 2005, 2006 include repetitive (e.g., daily) performing of extensions and contractions. Where the extensions/contractions may be of the same magnitude (e.g., 0.1-0.5 mm, or 0.1-0.3 mm, or about 0.25 mm magnitude, or lower or higher or intermediate magnitudes or ranges). In some embodiments, one or more of (e.g., each) strut movement (extension and/or contraction) is performed until verification that a sufficient force has been applied e.g., verification where a threshold current consumption value is reached e.g., once and/or a specified number of times.

In some embodiments, extensions and contractions (e.g., of an accordion movement actuation plan) are selected based on desired tissue movements. For example, where spatial relationships between tissue (e.g., bone tissue) and adjustable fixation device portion/s are used to determine individual strut movements to provide the desired tissue movement.

In some embodiments, strut extension and contraction feature/s (e.g., including one or more of magnitude of the extension/contraction, speed of movement, timing) are selected directly (e.g., and not determined based on tissue position with respect to the struts).

Referring now to FIG. 20B, at 2008, in some embodiments, upon verification that the tissue is sufficiently postoperatively healed for a start to bone positioning movements, a bone positioning actuation plan is implemented. In some embodiments, the verification is displayed to a user (e.g., HCP) who then may enable (e.g., via a user interface) initiation of the bone positioning actuation plan.

At 2009a, optionally, actual strut dimensions are monitored. For example, where measurements indicative of strut length are acquired. In some embodiments, the measurements are provided by encoders, for example, an encoder at one or more strut (e.g., and encoder at each strut providing a measurement for the corresponding strut). For example, as described regarding encoders 713 FIG. 7.

At 2009b strut dimension measurements are assessed, to determine discrepancies between expected strut length and/or movement and actual strut length and/or movement (e.g., as indicated by the measurements). Where the expected strut length and/or movement is that of the actuation plan (e.g., bone positioning actuation plan) e.g., as ideally implemented at the struts by the actuators.

At 2009b, optionally, if a discrepancy is determined, compensation movement/s are performed. For example, in following bone positioning and/or accordion movements.

For example, if it is identified that a bone positioning discrepancy exists in that a strut is shorter than it should be according to the actuation plan, a following accordion maneuver may be adjusted to implement the lacking length. For example, if the accordion maneuver, according to the accordion maneuver actuation plan, would not provide a net strut length change, the accordion maneuver (e.g., contraction movement/s reduced) is adjusted to provide a compensating net strut length change.

Assessment of discrepancies and/or implementation of compensation may be performed per bone positioning and/or accordion movement, or may be performed periodically e.g., when the discrepancy has reached a threshold value.

In some embodiments, each bone positioning actuation may include up to a few missed encoder steps, e.g., 1-20, or 0-10, or about 5 encoder steps, or lower or higher or intermediate numbers of steps. Where each bone positioning actuation may include 0.5-10 microns, or lower, or higher, or intermediate discrepancy e.g., where each encoder step corresponds to ~0.7 micron.

At 2010, in some embodiments, optionally concurrently to performance of step 2006, an accordion maneuver actuation plan is implemented. The accordion maneuver actuation plan, for example, including one or more feature as described regarding and/or illustrated in one or more of FIGS. 10A-C, and FIGS. 11-16.

At 2012, optionally, in some embodiments, tissue testing measurement/s are acquired e.g., during strut actuation/s. Where, the tissue testing measurements, for example, include one or more feature as described regarding step 1702 FIG. 17.

At 2014, in some embodiments, completion of bone repositioning is verified, for example, as verified by an HCP and/or by a completion of the bone positioning actuation plan. In some embodiments, if bone repositioning is not complete one or more of steps 2008-2014 are re-performed and/or continue to be performed.

At 2016, in some embodiments, tissue testing measurements are acquired, using strut actuations. Where, in some embodiments, the actuations are actuations of consolidation phase accordion maneuver plan. Alternatively, the actuations may be specific tissue testing actuations, for example, as described regarding step 2004.

At 2018, in some embodiments, measurements acquired at step 2016 are evaluated. Where the evaluation may include comparing the measurements with a threshold received at step 2002 and/or may include evaluating a change in measurement values with time (e.g., as described regarding FIG. 22). Where the threshold for At 2020, in some embodiments, the fixation device is removed, based on the evaluation at step 2018. For example, in some embodiments, based on the evaluation an indication of tissue status may be displayed to a user e.g., via a user interface. Where an HCP, based on the tissue status may then remove the fixation device.

Exemplary Force Feedback

FIG. 21 is a simplified schematic plot 2100 of strut length with time, according to some embodiments of the disclosure.

In some embodiments, FIG. 21 illustrates strut length with time, during an exemplary treatment period. In some embodiments, dynamization actuations 2104 occur during an initial period 2106 of treatment (e.g., during or after a latency period after a surgical procedure). Additionally, or alternatively, in some embodiments, dynamization activations 2102 occur during a bone positioning period 2108 of treatment e.g., where during the bone repositioning, bone positioning actuations 2102 are performed. Additionally, or alternatively, in some embodiments, dynamization activations 2102 occur during a consolidation period 2110 of treatment.

In some embodiments, treatment includes moving a single strut of an adjustable fixation device according to feature/s of plot 2100. In some embodiments, more than one strut is moved according to plot 2100. In some embodiments, plot 2100 illustrates relative movement between first and second fixation elements of the adjustable fixation device and/or of bone tissue (e.g., along an axis of the bone tissue) where a plurality of struts of the device are activated (e.g., concurrently) to produce the movements of plot 2100.

FIG. 22 is a simplified schematic plot 2200 of an indication of applied force with time, according to some embodiments of the disclosure.

In some embodiments, plot 2100 illustrates an indication applied force, with time, during an exemplary treatment. Where, in some embodiments, FIG. 22 corresponds to the treatment illustrated in FIG. 21 e.g., with the time scales aligned. The applied force data points illustrated may correspond to that applied by struts of an external fixation device in repositioning of bone tissue using the external fixation device.

For example, in an initial period 2108 (e.g., corresponding to initial period 2106) applied forces may be are low, for example, the low forces associated with low tissue density and/or connectivity e.g., of bone and/or soft tissue at the treatment site. Where, for example, to perform dynamization activations, little force is required to move the strut/s as tissue provides little resistance.

In some embodiments, for example, as tissue heals and/or bone osteogenesis occurs, potentially accelerated by dynamization activations, force required e.g., to perform the same amplitude and/or frequency dynamization actuations may rise e.g., over a threshold value 2202. Optionally, in some embodiments, upon verifying that sufficient tissue healing has occurred a bone positioning period 2208 (e.g., corresponding with bone positioning period 2108) is initiated. Where sufficient tissue healing is verified e.g., the verifying including verifying that the indication of force applied has increased sufficiently (e.g., from a previous level) and/or comparing the force applied with a threshold 2204 and/or evaluating fluctuation in force applied with time.

After completion of bone positioning, during a consolidation period 2210 (e.g., corresponding to consolidation period 2110) applied forces during dynamization activations may increase, and then plateau 2106, where data values have lower variation between data points. Where plateau 2106 may be associated with increasing density of bone tissue e.g., at the treatment site. Optionally, in some embodiments, the adjustable fixation device may be loosening and/or removed, based on the indication of force measurements during consolidation 2210. For example, upon verifying sufficient tissue healing. Where the verifying may include verifying that the indication of force applied has increased sufficiently (e.g., from a previous level) and/or comparing the indication of force applied with a threshold 2204 and/or evaluating fluctuation in the indication of force applied with time.

FIG. 23 is a simplified schematic plot 2300 of an indication of applied force with time, according to some embodiments of the disclosure.

In some embodiments, FIG. 23 illustrates force measured during an initial strut extension actuation 2302, a strut contraction actuation 2304, and a portion of an additional strut extension actuation 2306. Where strut movements may be part of a set of dynamization actuations. Each set may have 2-20, or 2-10, or lower or higher or intermediate numbers of actuations.

In some embodiments, an initial portion 2308 of an actuation may correspond to a rapid increase in force applied e.g., associated with initial resistance of tissue to movement e.g., where bone tissue growth connecting bone portions at the treatment site is separated. In some embodiments, during the initial portion, tissue may not move. As actuation 2302 continues, force applied may reduce e.g., associated with reduced tissue resistance. At initiation of compression actuation 2304 force required may be low e.g., as recently separated and/or stretched and/or tensioned tissue may present low resistance to movement to return it to a previous position. Force may rise to a peak 2312 magnitude e.g., where tissue resistance is high enough so that no movement occurs. In some embodiments, the compressive actuation may continue for a compressive force time period 2310. In some embodiments, subsequent extension 2306 may exhibit lower forces (e.g., peak 2316 being lower than peak 2314).

Referring back to FIG. 22, the indication of force plotted may relate to peak 2314 for one or an average of peak measurements for a plurality of actuators. The indication of force plotted may relate to an average current consumption over time for one or more portion of an actuation e.g., for a single strut or for a plurality of struts which may, for example, be concurrently moving to provide a movement between fixation elements.

GENERAL

As used within this document, the term "about" refers to ±20%

The terms "comprises", "comprising", "includes", "including", "having" and their conjugates mean "including but not limited to".

The term "consisting of" means "including and limited to".

As used herein, singular forms, for example, "a", "an" and "the" include plural references unless the context clearly dictates otherwise.

Within this application, various quantifications and/or expressions may include use of ranges. Range format should not be construed as an inflexible limitation on the scope of the present disclosure. Accordingly, descriptions including ranges should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within the stated range and/or subrange, for example, 1, 2, 3, 4, 5, and 6. Whenever a numerical range is indicated within this document, it is meant to include any cited numeral (fractional or integral) within the indicated range.

It is appreciated that certain features which are (e.g., for clarity) described in the context of separate embodiments, may also be provided in combination in a single embodiment. Where various features of the present disclosure, which are (e.g., for brevity) described in a context of a single embodiment, may also be provided separately or in any suitable sub-combination or may be suitable for use with any other described embodiment. Features described in the context of various embodiments are not to be considered essential features of those embodiments, unless the embodiment is inoperative without those elements.

Although the present disclosure has been described in conjunction with specific embodiments thereof, it is evident that many alternatives, modifications, and variations will be apparent to those skilled in the art. Accordingly, this application intends to embrace all such alternatives, modifications and variations that fall within the spirit and broad scope of the appended claims.

All references (e.g., publications, patents, patent applications) mentioned in this specification are herein incorporated in their entirety by reference into the specification, e.g., as if each individual publication, patent, or patent application was individually indicated to be incorporated herein by reference. Citation or identification of any reference in this application should not be construed as an admission that such reference is available as prior art to the present disclosure. In addition, any priority document(s) and/or documents related to this application (e.g., co-filed) are hereby incorporated herein by reference in its/their entirety.

Where section headings are used in this document, they should not be interpreted as necessarily limiting.

What is claimed is:

1. A control system for use with an adjustable bone fixation device including a first fixation element and a second fixation element connectable to bone tissue portions either side of a treatment site, the control system comprising:
  one or more actuators configured to controllably adjust lengths of a plurality of adjustable length struts of the bone fixation device, the plurality of adjustable lengths struts connecting said first and said second fixation elements of the bone fixation device, wherein length adjustment thereof changes a spatial relationship between said first and said second fixation elements; and
  circuitry configured to control said one or more actuators to cause said first and second fixation elements to perform an accordion maneuver by performing a plurality of actuations to adjust lengths of said plurality of adjustable length struts to create a reciprocal movement of said first and second fixation elements relative to each other.

2. The control system according to claim 1, wherein said one or more actuators comprise a plurality of actuators, each actuator of said plurality of actuators configured to controllably adjust a length of a strut of said plurality of adjustable length struts.

3. The control system according to claim 2, wherein said circuitry is configured to create said reciprocal movement by controlling at least two actuators of said plurality of actuators to simultaneously adjust the length of at least two associated struts to move said first and said second fixation elements relative to each other.

4. The control system according to claim 3, wherein said reciprocal movement of said first and second fixation elements comprises an expansion of a distance between the first and second fixation elements and a contraction of the distance between the first and second fixation elements, and wherein said reciprocal movement of said first and second fixation elements is configured to provide a reciprocal movement to said bone tissue portions.

5. The control system according to claim 1, wherein said circuitry is configured to:
  receive a model including spatial relationships between at least said bone tissue portions, said plurality of adjustable length struts, and said first and said second fixation elements; and
  control said plurality of actuations to provide said reciprocal movement to said bone tissue portions, based on said spatial relationships.

6. The control system according to claim 5, wherein said first fixation element is configured to be anchored to bone tissue by at least two first rigid connectors that are configured to extend from the fixation element into bone tissue, where said first fixation element and said at least two first rigid connectors are sized and shaped such that and connection between said first fixation element and said at least two first rigid connectors is such that said rigid first connectors are configured to extend into said bone tissue from different approach angles;
  wherein said spatial relationships include spatial relationships between said at least two first rigid connectors, said plurality of adjustable length struts, and said first and said second fixation elements.

7. The control system according to claim 6, wherein said reciprocal movement comprises oscillating movement of said first and second fixation elements relative to each other.

8. The control system according to claim 6, wherein said plurality of actuations includes a repeating pattern of strut actuations, where repetition is at a frequency of 1-3 Hz to mimic physiological forces experienced by bone tissue during walking.

9. The control system according to claim 6, wherein said plurality of actuations are such that said spatial relationship between said first and second fixation elements is the same prior to said plurality of actuations and after said plurality of actuations, which plurality of actuations are configured to maintain said bone tissue in an initial position.

10. The control system according to claim 1,
  wherein at least one of said plurality of actuations adjusts said spatial relationship to be configured to apply tensile force to bone tissue at a treatment site,
  wherein at least one of said plurality of actuations adjusts said spatial relationship to be configured to apply compressive force to said bone tissue at said treatment site.

11. The control system according to claim 1, wherein said control system comprises one or more sensors configured to generate one or more sensor signals comprising one or more of:
  a first sensor signal indicative of an axial force applied by one or more adjustable length struts of said plurality of adjustable length struts during one more of said plurality of actuations or bone positioning actuations; and
  a second sensor signal of said one or more sensor signals is indicative of a change in dimension of one or more adjustable length struts of said plurality of adjustable length struts during one or more of said plurality of actuations or said bone positioning actuations.

12. The control system according to claim 11, wherein said circuitry is configured to one or more of:
  control one or more of said plurality of actuations or said bone positioning actuations based on said one or more sensor signals; or
  determine one or more tissue features, based on said one or more sensor signals.

13. The control system according to claim 12, wherein said tissue features comprise whether bone movement has occurred during an actuation.

14. The control system according to claim 12, wherein said circuitry is configured to perform one or more of said plurality of actuations until said one or more sensor signals produced by said one or more sensors reaches a threshold value.

15. The control system according to claim 12, wherein said circuitry is configured to determine, from said one or more sensor signals:
  an amplitude of the change in dimension of the one or more adjustable length struts; and
  a speed of the change in dimension of the one or more adjustable length struts.

16. An adjustable bone fixation device comprising:
  a first fixation element;
  a second fixation element;
  a plurality of adjustable length struts; and
  a control system comprising:
    one or more actuators configured to controllably adjust lengths of a plurality of adjustable length struts of the bone fixation device, the plurality of adjustable length struts connecting said first and said second fixation elements of the bone fixation device, wherein length adjustment thereof changes a spatial relationship between said first and said second fixation elements; and
    circuitry configured to control said one or more actuators to cause said first and second fixation elements to perform an accordion maneuver by performing a plurality of actuations to adjust the lengths of said adjustable length struts to create a reciprocal movement of said first and second fixation elements relative to each other;

wherein planes of said first and said second fixation elements are configured to be orientated generally orthogonally to a central longitudinal axis of bone tissue; and wherein said first and said second fixation elements are sized and shaped to be configured to externally surround at least a third of a cross sectional circumference of said bone tissue, said cross section taken perpendicular to said central longitudinal axis.

17. A method of treatment comprising:

connecting a first fixation element and a second fixation element of an adjustable bone fixation device to different portions of bone tissue, on either side of a treatment site, the first and second fixation elements connected by a plurality of adjustable length rigid struts, adjustable by actuation of one or more actuators; and automatically actuating said one or more actuators a plurality of times to reciprocally adjust lengths of said plurality of adjustable length rigid struts to perform an accordion maneuver where said first and said second fixation elements move reciprocally relative to each other.

18. The method according to claim 17, comprising:

receiving one or more measurement signals indicative of axial forces applied by said plurality of adjustable length rigid struts, during said automatically actuating; and determining one or more tissue parameters, based on said one or more measurement signals.

19. The method according to claim 18, wherein said determining comprises:

receiving a three-dimensional (3D) model depicting spatial relationships between said different portions of bone tissue and one or more portions of the adjustable bone fixation device;

identifying, from the plurality of adjustable length rigid struts, an adjustable length rigid strut most axially aligned with a treatment site on the bone tissue based on the 3D model; and determining said one or more tissue parameters based on a measurement signal of said one or more measurement signals, which measurement signal is associated with said adjustable length rigid strut most axially aligned with said treatment site.

20. The method according to claim 18, wherein said one or more tissue parameters comprise a measure of ossification of tissue at said treatment site;

wherein the method comprises:

evaluating said measure of ossification; and generating an indication as to whether bone tissue is sufficiently healthy to:

initiate or resume bone repositioning; or remove the adjustable bone fixation device.

* * * * *